US008600519B2

(12) United States Patent
Stevenson et al.

(10) Patent No.: US 8,600,519 B2
(45) Date of Patent: Dec. 3, 2013

(54) TRANSIENT VOLTAGE/CURRENT PROTECTION SYSTEM FOR ELECTRONIC CIRCUITS ASSOCIATED WITH IMPLANTED LEADS

(75) Inventors: Robert A. Stevenson, Canyon Country, CA (US); Warren S. Dabney, Orchard Park, NY (US); Buehl E. Truex, Glendora, CA (US); Scott Brainard, Columbia Heights, MN (US); Henry R. Halperin, Pikesville, MD (US); Albert C. Lardo, Baltimore, MD (US)

(73) Assignee: Greatbatch Ltd., Clarence, NY (US)

( * ) Notice: Subject to any disclaimer, the term of this patent is extended or adjusted under 35 U.S.C. 154(b) by 404 days.

(21) Appl. No.: 12/497,424

(22) Filed: Jul. 2, 2009

(65) Prior Publication Data

US 2010/0023095 A1    Jan. 28, 2010

Related U.S. Application Data

(63) Continuation-in-part of application No. 10/123,534, filed on Apr. 15, 2002, now Pat. No. 7,844,319.

(60) Provisional application No. 61/079,693, filed on Jul. 10, 2008, provisional application No. 60/283,725, filed on Apr. 13, 2001, provisional application No. 61/144,377, filed on Jan. 13, 2009.

(51) Int. Cl.
*A61N 1/00* (2006.01)
(52) U.S. Cl.
USPC .......................................................... 607/116
(58) Field of Classification Search
USPC .......................................................... 607/63
See application file for complete search history.

(56) References Cited

U.S. PATENT DOCUMENTS

| 3,365,617 | A | 1/1968 | Flanagan |
| 3,471,748 | A | 10/1969 | Shiomi |
| 3,842,374 | A | 10/1974 | Schlicke |
| 4,021,759 | A | 5/1977 | Campi |
| 4,295,467 | A | 10/1981 | Mann et al. |
| 4,431,005 | A | 2/1984 | McCormick |
| 4,440,172 | A | 4/1984 | Langer |
| 4,445,501 | A | 5/1984 | Bresler |
| 4,572,198 | A | 2/1986 | Codrington |
| 4,643,186 | A | 2/1987 | Rosen et al. |

(Continued)

FOREIGN PATENT DOCUMENTS

| EP | 466424 A1 | 1/1992 |
| EP | 557127 A2 | 8/1993 |

(Continued)

OTHER PUBLICATIONS

European Patent Office, Extended European Search Report for EP 09008970.7-1269, Aug. 11, 2010.

*Primary Examiner* — Eric D. Bertram
*Assistant Examiner* — Roland Dinga
(74) *Attorney, Agent, or Firm* — Michael F. Scalise

(57) ABSTRACT

A transient voltage/surge current protection system is provided for electronic circuits associated with implanted leads. In particular, a transient voltage suppressor such as a diode, a zener diode, a transorb, a surge protector, varistor components or the like, is placed in parallel with the electronic circuits to thereby divert harmful surge current and bypass the electronic circuit during an external defibrillation event or during an applied therapeutic shock, such as from an ICD.

28 Claims, 20 Drawing Sheets

(56) References Cited

U.S. PATENT DOCUMENTS

| | | |
|---|---|---|
| 4,672,972 A | 6/1987 | Berke |
| 4,745,923 A | 5/1988 | Winstrom |
| 4,754,752 A | 7/1988 | Ginsburg et al. |
| 4,757,820 A | 7/1988 | Itoh |
| 4,766,381 A | 8/1988 | Conturo et al. |
| 4,813,429 A | 3/1989 | Eshel et al. |
| 4,823,812 A | 4/1989 | Eshel et al. |
| 4,832,023 A | 5/1989 | Murphy-Chutorian et al. |
| 4,859,950 A | 8/1989 | Keren |
| 4,932,411 A | 6/1990 | Fritschy et al. |
| 4,960,106 A | 10/1990 | Kubokawa |
| 4,989,608 A | 2/1991 | Ratner |
| 5,019,075 A | 5/1991 | Spears et al. |
| 5,095,911 A | 3/1992 | Pomeranz |
| 5,099,208 A | 3/1992 | Fitzpatrick et al. |
| 5,167,233 A | 12/1992 | Eberle et al. |
| 5,170,806 A | 12/1992 | Colen |
| 5,178,618 A | 1/1993 | Kandarpa |
| 5,190,046 A | 3/1993 | Shturman |
| 5,211,165 A | 5/1993 | Dumoulin et al. |
| 5,217,010 A * | 6/1993 | Tsitlik et al. .................... 607/9 |
| 5,266,079 A | 11/1993 | Iga |
| 5,271,400 A | 12/1993 | Dumoulin et al. |
| 5,307,808 A | 5/1994 | Dumoulin et al. |
| 5,307,814 A | 5/1994 | Kressel et al. |
| 5,318,025 A | 6/1994 | Dumoulin et al. |
| 5,323,776 A | 6/1994 | Blakeley et al. |
| 5,323,778 A | 6/1994 | Kandarpa et al. |
| 5,334,193 A | 8/1994 | Nardella |
| 5,336,253 A * | 8/1994 | Gordon et al. ................ 607/122 |
| 5,348,010 A | 9/1994 | Schnall et al. |
| 5,352,979 A | 10/1994 | Conturo |
| 5,358,515 A | 10/1994 | Hurter et al. |
| 5,365,928 A | 11/1994 | Rhinehart et al. |
| 5,369,390 A | 11/1994 | Lin et al. |
| 5,370,644 A | 12/1994 | Langberg |
| 5,400,787 A | 3/1995 | Marandos |
| 5,413,104 A | 5/1995 | Buijs et al. |
| 5,419,325 A | 5/1995 | Dumoulin et al. |
| 5,433,717 A | 7/1995 | Rubinsky et al. |
| 5,437,277 A | 8/1995 | Dumoulin et al. |
| 5,443,066 A | 8/1995 | Dumoulin et al. |
| 5,443,489 A | 8/1995 | Ben-Haim |
| 5,447,156 A | 9/1995 | Dumoulin et al. |
| 5,451,232 A | 9/1995 | Rhinehart et al. |
| 5,462,055 A | 10/1995 | Casey et al. |
| 5,476,095 A | 12/1995 | Schnall et al. |
| 5,498,261 A | 3/1996 | Strul |
| 5,507,743 A | 4/1996 | Edwards et al. |
| 5,512,825 A | 4/1996 | Atalar et al. |
| 5,531,782 A | 7/1996 | Kroll et al. |
| 5,540,679 A | 7/1996 | Fram et al. |
| 5,545,183 A | 8/1996 | Altman |
| 5,558,093 A | 9/1996 | Pomeranz |
| 5,578,008 A | 11/1996 | Hara |
| 5,584,870 A * | 12/1996 | Single et al. .................... 607/63 |
| 5,588,432 A | 12/1996 | Crowley |
| 5,590,657 A | 1/1997 | Cain et al. |
| 5,623,241 A | 4/1997 | Minkoff |
| 5,662,108 A | 9/1997 | Budd et al. |
| 5,682,897 A | 11/1997 | Pomeranz |
| 5,685,878 A | 11/1997 | Falwell et al. |
| 5,699,801 A | 12/1997 | Atalar et al. |
| 5,706,810 A | 1/1998 | Rubinsky et al. |
| 5,715,825 A | 2/1998 | Crowley |
| 5,769,800 A | 6/1998 | Gelfand et al. |
| 5,772,689 A | 6/1998 | Kroll |
| 5,775,338 A | 7/1998 | Hastings |
| 5,779,669 A | 7/1998 | Haissaguerre et al. |
| 5,792,055 A | 8/1998 | McKinnon |
| 5,797,970 A * | 8/1998 | Pouvreau .......................... 607/9 |
| 5,833,608 A | 11/1998 | Acker |
| 5,836,992 A | 11/1998 | Thompson et al. |
| 5,840,031 A | 11/1998 | Crowley |
| 5,864,234 A | 1/1999 | Ludeke |
| 5,868,674 A | 2/1999 | Glowinski et al. |
| 5,870,273 A | 2/1999 | Sogabe et al. |
| 5,879,347 A | 3/1999 | Saadat |
| 5,891,134 A | 4/1999 | Goble et al. |
| 5,916,162 A | 6/1999 | Snelten et al. |
| 5,928,145 A | 7/1999 | Ocali et al. |
| 5,928,159 A | 7/1999 | Eggers et al. |
| 5,938,609 A | 8/1999 | Pomeranz |
| 5,938,692 A | 8/1999 | Rudie |
| 5,964,705 A | 10/1999 | Truwitt et al. |
| 5,968,086 A | 10/1999 | Bonner et al. |
| 5,999,398 A | 12/1999 | Maki |
| 6,004,269 A | 12/1999 | Crowley et al. |
| 6,011,995 A | 1/2000 | Guglielmi et al. |
| 6,026,316 A | 2/2000 | Kucharczyk et al. |
| 6,027,500 A | 2/2000 | Buckles et al. |
| 6,031,375 A | 2/2000 | Atalar et al. |
| 6,045,532 A | 4/2000 | Eggers et al. |
| 6,052,623 A * | 4/2000 | Fenner et al. ................... 607/36 |
| 6,066,136 A | 5/2000 | Geistert |
| 6,128,522 A | 10/2000 | Acker et al. |
| 6,129,670 A | 10/2000 | Burdette et al. |
| 6,171,240 B1 | 1/2001 | Young et al. |
| 6,171,241 B1 | 1/2001 | McVeigh et al. |
| 6,188,219 B1 | 2/2001 | Reeder et al. |
| 6,226,545 B1 | 5/2001 | Gilderdale |
| 6,238,390 B1 | 5/2001 | Tu et al. |
| 6,263,229 B1 | 7/2001 | Atalar et al. |
| 6,272,370 B1 | 8/2001 | Gillies et al. |
| 6,284,971 B1 | 9/2001 | Atalar et al. |
| 6,314,325 B1 * | 11/2001 | Fitz ................................ 607/46 |
| 6,327,498 B1 | 12/2001 | Kroll |
| 6,332,089 B1 | 12/2001 | Acker et al. |
| 6,351,368 B1 | 2/2002 | Kim |
| 6,390,996 B1 | 5/2002 | Halperin et al. |
| 6,408,202 B1 | 6/2002 | Lima et al. |
| 6,418,348 B1 | 7/2002 | Witte |
| 6,428,537 B1 | 8/2002 | Swanson et al. |
| 6,459,935 B1 | 10/2002 | Piersma |
| 6,549,800 B1 | 4/2003 | Atalar et al. |
| 6,556,009 B2 | 4/2003 | Kellman et al. |
| 6,593,884 B1 | 7/2003 | Gilboae et al. |
| 6,606,513 B2 | 8/2003 | Lardo et al. |
| 6,628,980 B2 | 9/2003 | Atalar et al. |
| 6,633,780 B1 | 10/2003 | Bergert et al. |
| 6,654,628 B1 | 11/2003 | Silber et al. |
| 6,675,033 B1 | 1/2004 | Lardo et al. |
| 6,690,963 B2 | 2/2004 | Ben-Haim et al. |
| 6,701,176 B1 | 3/2004 | Halperin et al. |
| 6,714,809 B2 | 3/2004 | Lee et al. |
| 6,771,067 B2 | 8/2004 | Kellman et al. |
| 6,898,454 B2 * | 5/2005 | Atalar et al. .................. 600/410 |
| 6,904,307 B2 | 6/2005 | Karmarkar et al. |
| 6,925,328 B2 * | 8/2005 | Foster et al. ..................... 607/9 |
| 6,985,775 B2 | 1/2006 | Reinke et al. |
| 7,155,271 B2 | 12/2006 | Halperin |
| 7,236,816 B2 | 6/2007 | Kumar et al. |
| 7,305,270 B1 | 12/2007 | Kroll et al. |
| 7,422,568 B2 | 9/2008 | Yang et al. |
| 7,620,453 B1 | 11/2009 | Propato et al. |
| 2002/0055678 A1 | 5/2002 | Scott et al. |
| 2002/0095187 A1 | 7/2002 | Thompson et al. |
| 2002/0095197 A1 | 7/2002 | Lardo et al. |
| 2002/0103523 A1 | 8/2002 | Helland et al. |
| 2002/0161402 A1 * | 10/2002 | Vogel et al. ....................... 607/1 |
| 2002/0177771 A1 | 11/2002 | Guttman et al. |
| 2002/0192688 A1 | 12/2002 | Yang et al. |
| 2003/0028095 A1 | 2/2003 | Tulley et al. |
| 2003/0050557 A1 | 3/2003 | Susil et al. |
| 2004/0015079 A1 | 1/2004 | Berger et al. |
| 2004/0095698 A1 * | 5/2004 | Gerrish et al. ................ 361/91.1 |
| 2006/0100506 A1 | 5/2006 | Halperin |
| 2006/0122679 A1 * | 6/2006 | Wengreen et al. ............. 607/122 |
| 2006/0247684 A1 | 11/2006 | Halperin et al. |
| 2007/0088416 A1 | 4/2007 | Atalar et al. |
| 2007/0173909 A1 | 7/2007 | Inman et al. |
| 2007/0233200 A1 * | 10/2007 | Maschke .......................... 607/9 |
| 2008/0058902 A1 | 3/2008 | Gray et al. |
| 2008/0183230 A1 | 7/2008 | Kemmetmueller et al. |

(56) References Cited

U.S. PATENT DOCUMENTS

FOREIGN PATENT DOCUMENTS

| | | |
|---|---|---|
| EP | 0 673 621 | 9/1995 |
| JP | 994238 | 4/1997 |
| WO | WO 8704080 | 7/1987 |
| WO | WO 9210213 | 6/1992 |
| WO | WO 9423782 | 10/1994 |
| WO | WO 9740396 | 10/1997 |
| WO | WO 9852461 | 11/1998 |
| WO | WO 0010456 | 3/2000 |
| WO | WO 0025672 | 5/2000 |
| WO | WO 02083016 | 10/2002 |
| WO | 2005/102446 A1 | 11/2005 |

\* cited by examiner

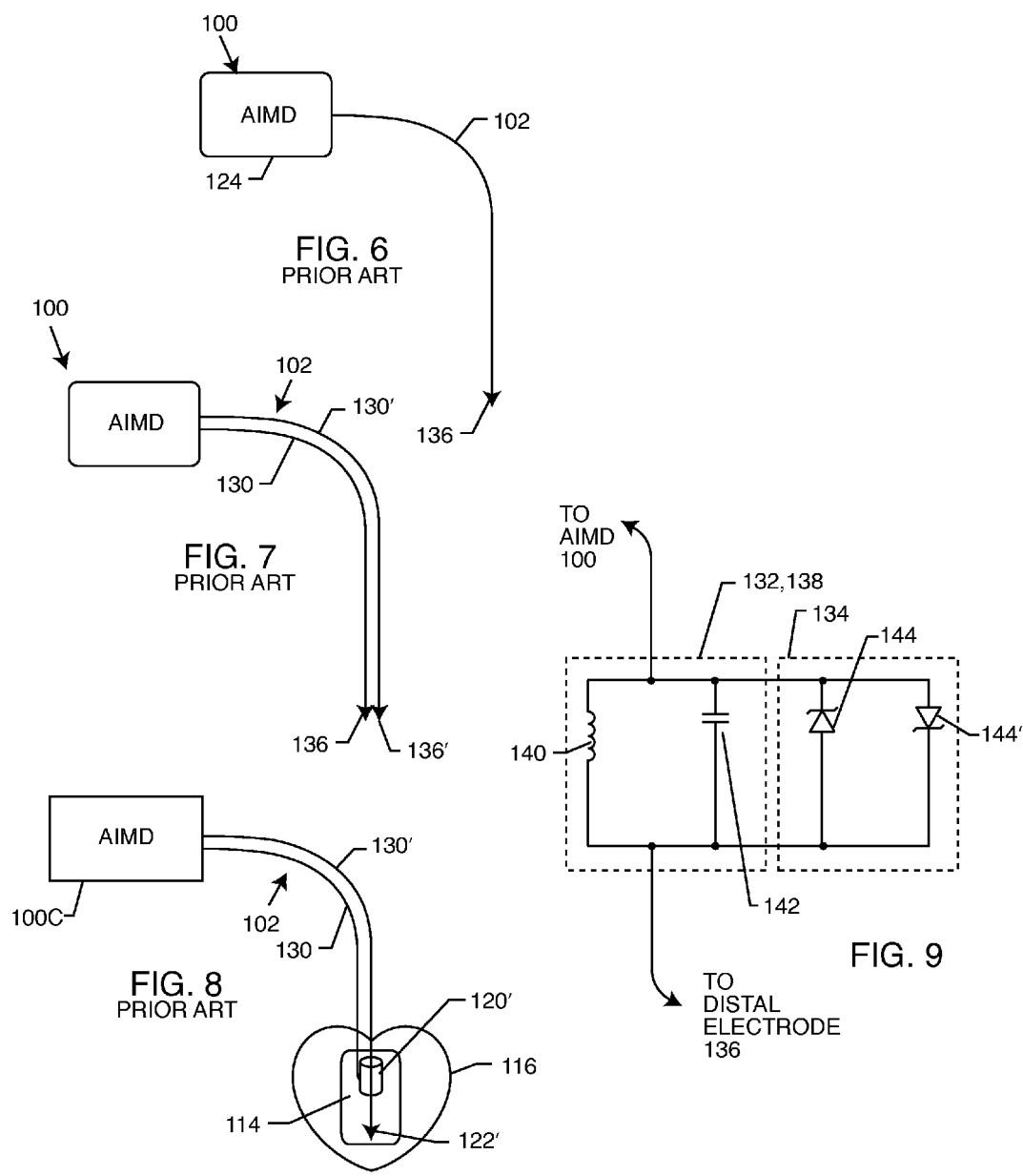

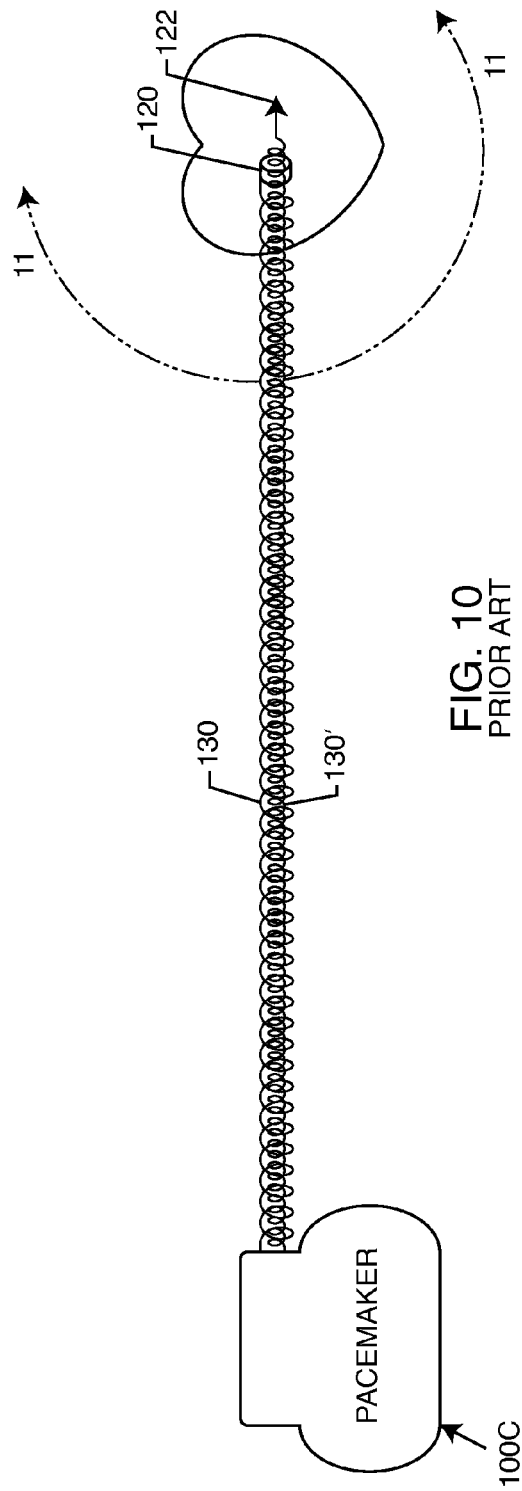
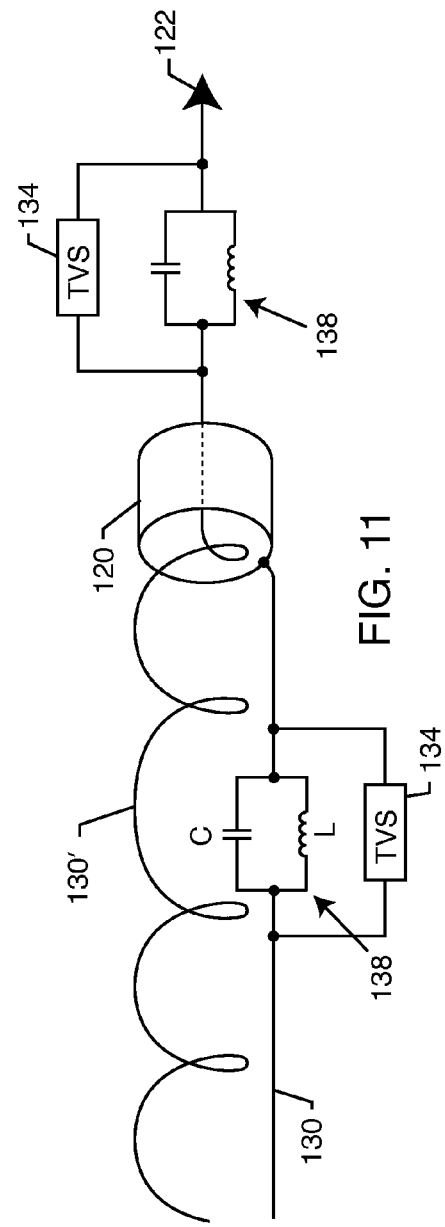
FIG. 10
PRIOR ART
FIG. 11

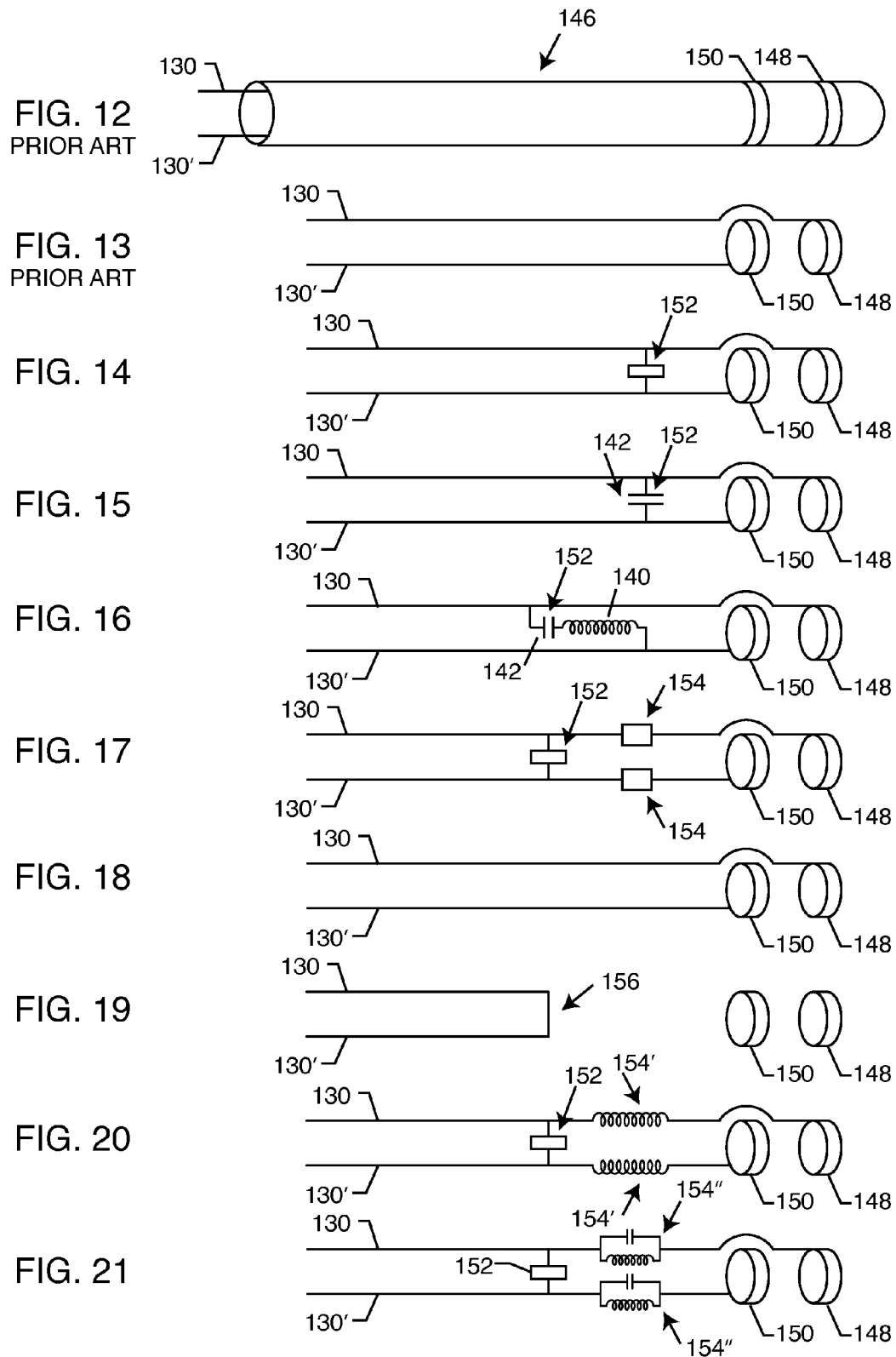

TRANSIENT VOLTAGE/CURRENT PROTECTION SYSTEM FOR ELECTRONIC CIRCUITS ASSOCIATED WITH IMPLANTED LEADS

BACKGROUND OF THE INVENTION

The present invention relates to electronic circuits associated with leads and leadwires disposed within a living body. More particularly, the present invention relates to a transient voltage/surge current protection system wherein a transient voltage suppressor is electrically connected in parallel with an electronic circuit in order to protect the circuit from a surge current which may momentarily develop as a result of, for example, the use of an automatic external defibrillator during a cardiac emergency.

Implanted leads or implanted leadwires are associated with a variety of active implantable medical devices (AIMDs), including cardiac pacemakers, implantable cardioverter defibrillators (ICDs), neurostimulators including deep brain stimulators, spinal cord stimulators and other types of pain control stimulators, and the like. Implanted leadwires may also be associated with probes or catheters which are temporarily inserted into the body. Probes and catheters are used for a variety of applications, including mapping of cardiac signals, cancer ablation and the like. In general, implanted leads or leadwires associated with AIMDs or elongated leads associated with probes or catheters have both a proximal end, external of the AIMD, and a distal therapy delivery or sensing end.

Automatic external defibrillators (AEDs) are now very common and appear in many public places, including government buildings, airports, airplanes, etc. AEDs are generally used by trained personnel who will attend to incidents, however many are public access units which can be found in places including corporate and government offices, shopping centers, airports, restaurants, casinos, hotels, sports stadiums, schools and universities, community centers, fitness centers and health clubs.

An increasing number of patients with AIMDs are undergoing external defibrillation during cardiac emergencies. There have been reports of damage to AIMDs due to use of AEDs during such emergencies. Typically, AIMDs include internal circuit protection devices to protect against these external voltage surges. Defibrillation is the definitive treatment for life-threatening cardiac arrhythmias, ventricular fibrillation and pulseless ventricular tachycardia. Defibrillation consists of delivering a therapeutic dose of electrical energy to the affected heart with a defibrillator device. The external defibrillator or AED produces a high energy which depolarizes a critical mass of the heart muscle, terminates the arrhythmia, and allows normal sinus rhythm to be re-established by the body's natural pacemaker in the sinoatrial of the heart. Defibrillators can be external, transvenous or implanted depending on the type of device used. External units, known as automatic external defibrillators (AEDs), automate the diagnosis of treatable rhythms so that lay responders or bystanders are able to use them successfully with little or, in some cases, no training.

For an adult, the nominal delivered pulse from an AED is 150 joules. For an infant or child, the nominal energy delivery is 50 joules. Studies have shown that a biphasic waveform of 115 joules is equivalent to a monophasic wave of about 200 joules. Because of the decreased energy needed, most defibrillators now use biphasic waveforms. The lower energy can result in both longer battery life and a shorter time to full charge for the AED. An AED can supply as much as 2000 volts from its high-energy storage capacitors with an 80 maximum peak ampere for a 25-ohm impedance patient. A 50-ohm patient would receive 40 maximum peak amperes (reference: Association for the Advancement of Medical Instrumentation Standards). The surge currents induced in an implanted leadwire due to the transient voltage introduced through use of an AED could be 2 to 6 amps or even higher.

In order to make AIMDs compatible with medical diagnostic procedures such as magnetic resonance imaging (MRI), a number of lead-based electronic components are being developed. These lead-based components can be bandstop filters, electronic filters, micro-electrical mechanical switches (MEMS), multiplexers, and other types of active electronic filters or switches. See, for example, U.S. Pat. No. 7,363,090 the contents of which are incorporated herein by reference. See also U.S. patent Ser. Nos. 11/558,349, 11/743,000, 11/860,402, 11/930,742, 11/838,035, 11/943,883, 11/943,854, 12/8,489,921, and 61/016,364 the contents all of which are incorporated herein by reference. During external defibrillation from an AED, high currents can be picked up by implanted leads or leadwires. This depends on electrode placement, the physical characteristics of the patient, and also the location of implanted leads or leadwires.

A transient voltage or high surge current need not always come from an external source like an AED. In fact, an implantable cardioverter defibrillator (ICD) senses abnormal cardiac activity, such as dangerous ventricular arrhythmias. When a dangerous ventricular arrhythmia is detected, the ICD delivers a high voltage shock through leads whose electrodes are in intimate contact or associated with the heart. If the ICD leadwire system has any electronic circuits disposed in its leads, the high voltage shock must pass through said electronic circuit. For example, if a bandstop filter, such as one described in U.S. Pat. No. 7,363,090, which shows inductor-capacitor electronic circuits in series with implanted leads, is placed in the high voltage shock delivery electrode circuit of an ICD, then the ICD pulse would have to pass through the bandstop filter. Since the ICD pulse is of a low frequency, the bulk of the pulse would pass through the inductor component of the bandstop filter. However, it is really not practical or feasible to make inductors with large enough wires to handle such high currents as an ICD pulse.

ICD pulses may be monophasic or biphasic. Therefore, it is important to protect circuit components placed in implanted leads from both positive and negative polarity voltage which could result in current surges in either direction in the lead. As for the case with an AED, protection of all kinds of lead based electronic circuits is important. This includes not only bandstop filters, but all types of frequency selective impeding or diverting circuits, MEMS switches, electronic switches, multiplexing switches and the like. Such protection is also needed for a wide range of lead based sensors, including oxygen sensors, pressure sensors, general blood gas sensors, artificial valve lead transducers and the like.

Accordingly, there is a need to provide circuit protection devices for electrical or electronic circuits that are associated with implanted or implantable leads, leadwires and the like. Such circuit protection devices must be of such dimension and construction to lend themselves for use with implantable leads, leadwires and the like, and must not interfere with the normal therapy delivery or sensing functions of the implanted leads or leadwires. Moreover, such circuit protection devices must allow for normal operation of the electrical or electronic circuits disposed in series with the implanted leads or leadwires, and preferably function to divert a surge current around the electrical or electronic circuits in order to bypass the same during a cardiac emergency, for example, a high voltage pulse introduced into the major leadwire system through the use of an AED or an ICD. The present invention fulfills these needs and provides other related advantages.

SUMMARY OF THE INVENTION

The present invention relates to a transient voltage/surge current protection system. The system includes a lead having a proximal end and a distal end disposed within a living body. An electronic circuit is associated with the lead between the proximal end and the distal end. The transient voltage suppressor is electrically connected in parallel with the electronic circuit.

The lead may comprise a probe, a catheter, or a leadwire connected to an active medical device. Further, the lead may either be temporarily or permanently implanted in a human body.

The electronic circuit comprises a frequency selective diverter (low impedance) or impeder (high impedance) circuits or combinations thereof. Such a frequency selective diverter or impeder circuit may comprise an electronic filter. This could be a low pass filter, an L-C trap filter, or a bandstop filter. Moreover, the electronic circuit may comprise micro electrical-mechanical switches (MEMS), passive electronic switches, multiplexing switches, active electronic switches, or diode switches.

The transient voltage suppressor may comprise a diode, a zener diode, a transorb, a surge protector, or varistor components. In a particularly preferred embodiment, the transient voltage suppressor comprises back-to-back or bi-directional components. The back-to-back components may comprise zener diodes.

In another embodiment, the electronic circuit comprises a capacitor having a first electrode plate separated from a second electrode plate by a dielectric material. The dielectric material comprises a varistor dielectric material so that the capacitor itself integrates features of the electronic circuit and the transient voltage suppressor.

A hermetic container may be provided in which the electronic circuit and/or the transient voltage suppressor is disposed.

The lead may include a therapy delivery or sensing electrode. In this case, the electronic circuit is closely associated with the therapy delivery or sensing electrode which may comprise a tip electrode and a ring electrode or a neurostimulator.

In another embodiment, the electronic circuit and the transient voltage suppressor comprise discrete components physically arranged in series, but electrically connected in parallel. For example, the electronic circuit can comprise a discrete capacitor and a discrete inductor physically arranged in series, but electrically connected in parallel. The transient voltage suppressor comprises a first diode physically arranged in series with the capacitor and the inductor, but electrically connected in parallel to each. The transient voltage suppressor may also comprise a discrete second diode physically arranged in series with the first diode, the capacitor and the inductor, and electrically connected in parallel to each.

A second transient voltage suppressor may be disposed adjacent to the proximal end of the lead. Such second transient voltage suppressor may comprise a fast-acting switch disposed within an active medical device associated with the lead.

Other features and advantages of the present invention will be apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 6 is a schematic illustration of a prior art unipolar AIMD system;

FIG. 7 is a schematic illustration of a prior art bipolar AIMD system;

FIG. 8 is a schematic illustration similar to FIG. 7 of a prior art bipolar cardiac pacemaker wherein the distal electrodes comprise a ring which floats in the blood pool and a distal tip active electrode;

FIG. 9 is an electrical schematic illustration of a bandstop filter with a transient voltage suppressor electrically connected in parallel in accordance with the present invention and configured for placement in either the distal ring electrode or the distal tip electrode shown in FIG. 8;

FIG. 10 is a schematic illustration of a prior art bipolar pacemaker system;

FIG. 11 is an enlarged schematic taken generally of the area indicated by the line 11-11 of FIG. 10, illustrating the presence of bandstop filters and their associated transient voltage suppressors (TVS) in series with the distal tip and the distal ring;

FIG. 12 is a diagrammatic view of a typical probe or catheter;

FIG. 13 is a diagrammatic view of the interior of the prober or catheter of FIG. 12;

FIG. 14 is an electrical circuit diagram of the structure shown in FIG. 13, with a general impedance element connected between leadwires;

FIG. 15 is an electrical diagrammatic view similar to FIG. 14, illustrating a capacitor representing a frequency dependent reactive element between the leadwires;

FIG. 16 is a view similar to FIG. 15, wherein the general reactance element has been replaced by a capacitor in series with an inductor;

FIG. 17 is a view similar to FIGS. 14-16, showing the addition of series frequency selective reactances;

FIG. 18 is similar to FIG. 13, showing a low frequency model of the catheter and associated leads described in FIG. 12;

FIG. 19 is a view similar to FIGS. 13-18, illustrating how the distal rings are electrically isolated at a high frequency;

FIG. 20 is a view similar to FIGS. 13-19, showing the addition of series inductor components added to the frequency selective elements 20;

FIG. 21 is similar to FIGS. 13-20, illustrating frequency selective elements which incorporate parallel resonant inductor and capacitor bandstop filters;

DETAILED DESCRIPTION OF THE PREFERRED EMBODIMENTS

As shown in drawings, for purposes of illustration, the present invention provides circuit protection devices for electrical or electronic circuits that are associated with implanted leads. In particular, the present invention provides circuit protection devices such as diodes, zener diodes, Transorbs, surge protectors, varistor components or the like, placed in parallel with electronic circuits in implanted leads to thereby divert harmful current away (around) from sensitive electronic components during an external (AED) or internal (ICD) defibrillation event.

Figure 1:
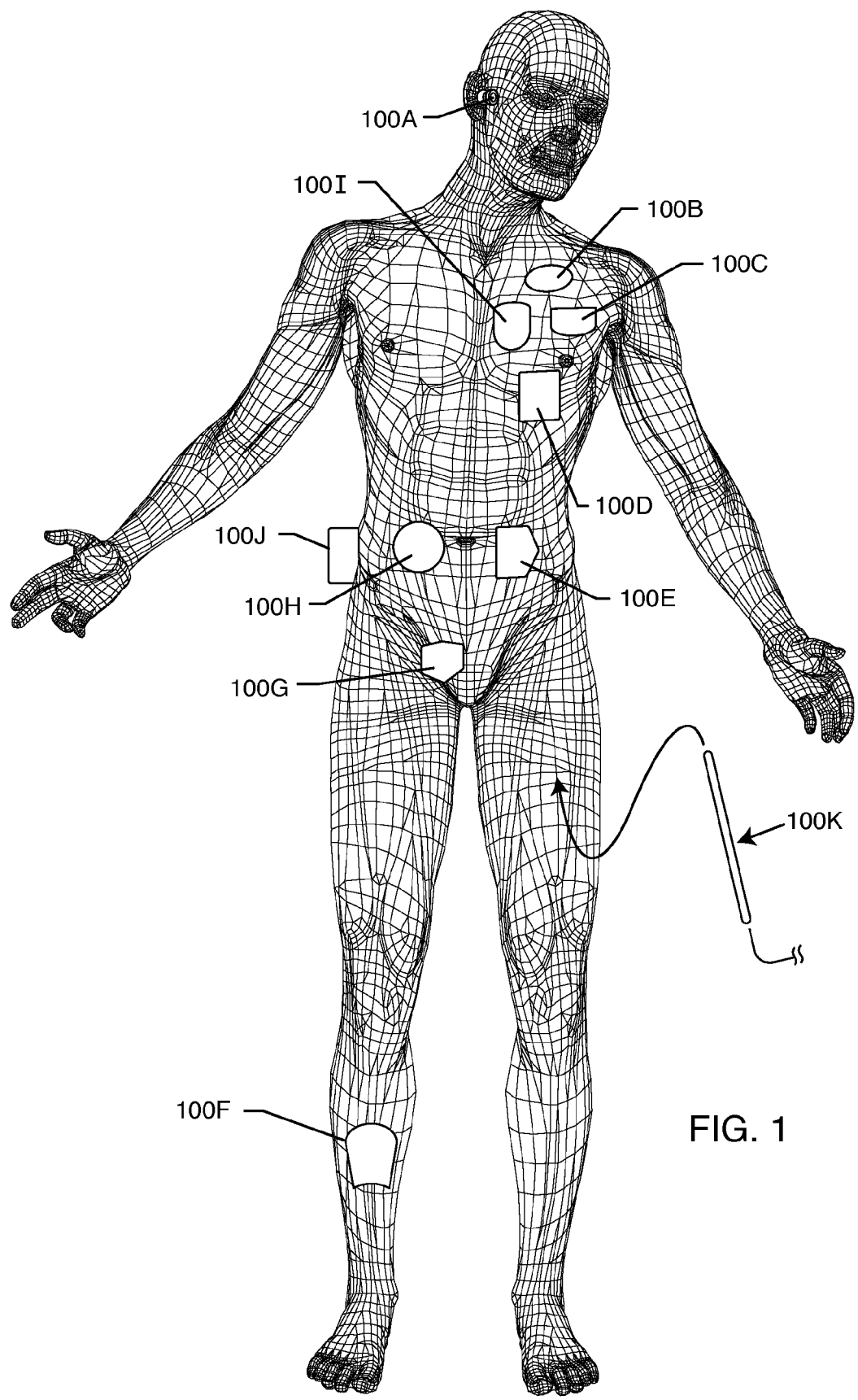
FIG. 1 is a wire-formed diagram of a generic human body showing a number of exemplary implanted medical devices.

FIG. 1 is a wire formed diagram of a generic human body showing a number of implanted medical devices 100A-K. 100A represents a family of hearing devices which can include the group of cochlear implants, piezoelectric sound bridge transducers and the like. 100B represents a variety of neurostimulators and brain stimulators. Neurostimulators are used to stimulate the Vagus nerve, for example, to treat epilepsy, obesity and depression. Brain stimulators are pacemaker-like devices and include electrodes implanted deep into the brain for sensing the onset of the seizure and also providing electrical stimulation to brain tissue to prevent the seizure from actually occurring. The leadwires associated with a deep brain stimulator are often placed using real time MRI imaging. Most commonly such leadwires are placed during real time MRI. 100C shows a cardiac pacemaker which is well-known in the art. 100D includes the family of left ventricular assist devices (LVAD's), and artificial hearts, including the recently introduced artificial heart known as the Abiocor. 100E includes an entire family of drug pumps which can be used for dispensing of insulin, chemotherapy drugs, pain medications and the like. Insulin pumps are evolving from passive devices to ones that have sensors and closed loop systems. That is, real time monitoring of blood sugar levels will occur. These devices tend to be more sensitive to EMI than passive pumps that have no sense circuitry or externally implanted leadwires. 100F includes a variety of bone growth stimulators for rapid healing of fractures. 100G includes urinary incontinence devices. 100H includes the family of pain relief spinal cord stimulators and anti-tremor stimulators. 100H also includes an entire family of other types of neurostimulators used to block pain. 100I includes a family of implantable cardioverter defibrillators (ICD) devices and also includes the family of congestive heart failure devices (CHF). This is also known in the art as cardio resynchronization therapy devices, otherwise known as CRT devices. 100J illustrates an externally worn pack. This pack could be an external insulin pump, an external drug pump, an external neurostimulator or even a ventricular assist device. 100K illustrates the insertion of an external probe or catheter. These probes can be inserted into the femoral artery, for example, or in any other number of locations in the human body.

Figure 2:
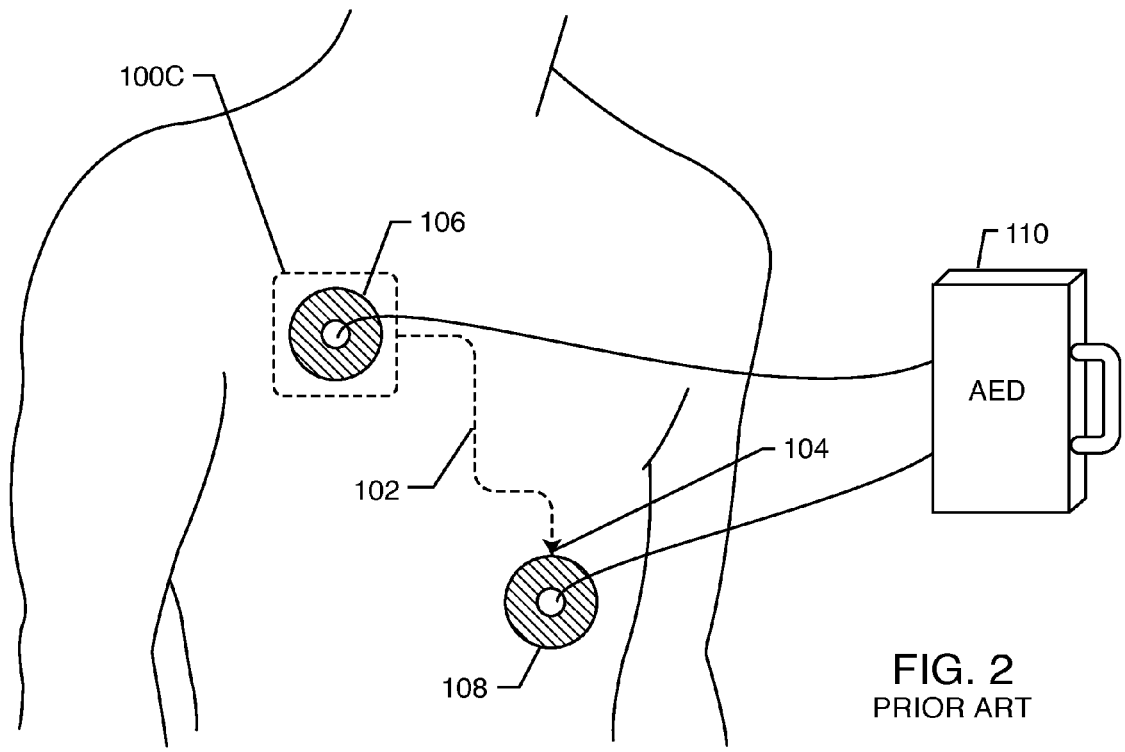
FIG. 2 is a outline illustration of the neck and torso of a typical patient who has an implanted active implantable medical device (AIMD), showing possible placement of AED paddles on the patient.

FIG. 2 is an outline drawing of the neck and torso of a typical patient who has an active implanted medical device (AIMD). In this case, by way of illustration, the AIMD is a pacemaker 100C. The pacemaker 100C has an implanted lead 102 which is directed to a distal electrode 104 which, in this case, would be typically implanted into the right ventricle of the patient's heart. The pacemaker 100C typically does sensing and also provides pacing pulses in order that the heart can properly beat. In case of a cardiac emergency, for example when the patient would stop breathing or stop having a heart beat, emergency personnel could place the two electrode paddles 106 and 108 of an automatic external defibrillator (AED) 110 as shown. When one carefully reads the instructions on the lid of the AED 110, it shows a diagram for correct placement of the paddles. Typically, one paddle would be placed down fairly low in the abdomen and the other paddle would be placed fairly high on the chest. However, in haste, emergency personnel often place one paddle directly over the pectoral pocket area of the cardiac pacemaker 100C and the other paddle directly over the right ventricle of the heart. When the paddles are placed in this (incorrect) location, maximum currents are induced into the implanted lead 102. These induced currents are undesirable as they could cause excessive currents to flow inside the pacemaker 100C thereby damaging lead-based sensitive electronic circuits. To protect against such surge currents from an AED 110, most AIMDs have internal circuit protection devices. However, it is now becoming quite common for electronic circuits to be placed in the lead 102 itself. Absent the present invention, there is no protection for these electronic components against the high voltage current surges caused from AEDs or AED events.

The implant location for the pacemaker 100C shown in FIG. 2 (the right pectoral pocket), is not the preferred location. A pacemaker 100C or ICD 100I is preferrably placed in the left pectoral pocket where the currents induced into lead 102 by an AED 110 would be lessened. However, there is still a significant number of patients who do have a right pectoral AIMD implant. The reasons for this include previous removal due to a pocket infection of the device with the necessity to place it on the other side, certain patients have two devices, and other patients have an implantable neurostimulator 100B in the same location for convenient access by tunneling up into the neck to the vagus nerve on the appropriate side.

Figure 3:
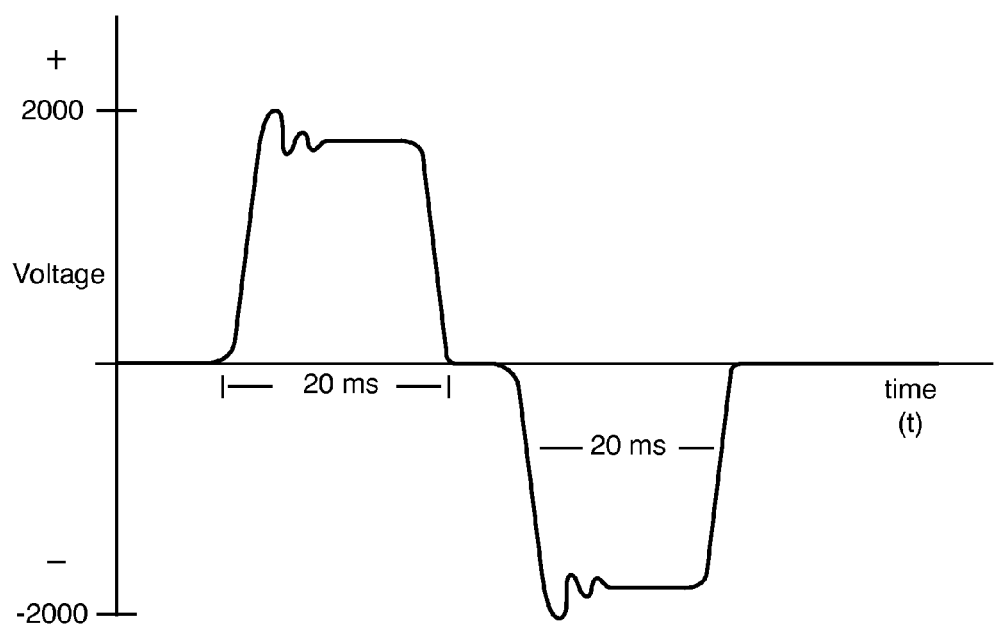
FIG. 3 is a graph illustrating a typical biphasic shock waveform that may be generated by the AED.

FIG. 3 shows a typical biphasic shock waveform where the AED voltage will vary from +2000 to −2000 volts. The timing of the pulses can vary greatly from one AED manufacturer to another. In one typical example, the positive going pulse would have a pulse width of 20 milliseconds. After a short dwell period, the negative pulse would also have a duration of approximately 20 milliseconds. The biphasic shock waveform of FIG. 3 could also represent the output pulse from an ICD. However, for an ICD, the voltage is typically lower (typically around 800 volts) because the implanted leads are directly connected to heart tissue. The AED has to provide higher energy since it is shocking through the chest wall, pectoral muscles and so forth. Therefore, an ICD is more efficient with its direct connection. However, in both cases, the transient voltage can result in very high surge currents which can be very damaging to active or passive lead-based electronic circuits.

Figure 4:
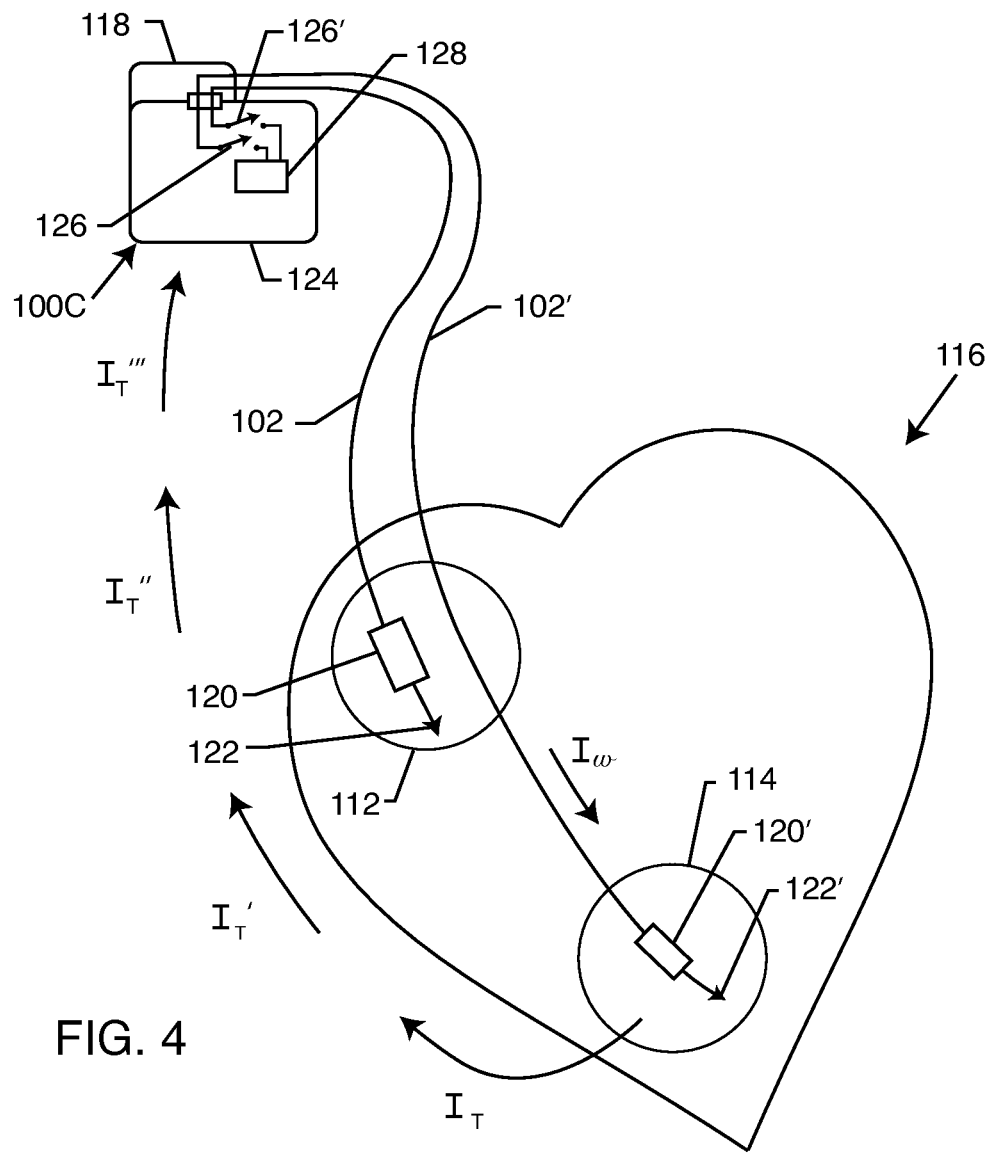
FIG. 4 is a schematic illustration of a human heart and a dual chamber, bipolar implanted cardiac pacemaker having leads embodying the present invention implanted in the heart.

FIG. 4 shows the right atrium 112 and right ventricle 114 of a typical human heart 116. A dual chamber bipolar implanted cardiac pacemaker 100C is shown which has a connector block 118 for convenient plugging in of implanted leads 102 and 102. In general, for pacemakers 100C and ICDs 100I, these connector blocks 118 are designated by ISO Standards IS-1, DF-1 or IS-4. A lead 102 is directed to the right atrium 112 and is a bipolar lead. At its distal end, it has a distal ring electrode 120 and a distal tip electrode 122. Another lead 102 is directed through epicardial placement into the right ventricle 114. It is also a bipolar lead which terminates in a ring electrode 120' and a tip electrode 122' as shown. When a biphasic shock is applied to the patient's skin via an AED 110, current loops are set up as energy is delivered to tissue. In general, the current $I_W$ would flow as shown and then have a return path $I_T$, $I_T'$, $I_T''$, and $I_T'''$ back to the conductive housing 124 which is typically conductive of the AIMD. It is the current $I_W$ that is of concern, particularly when there are electronic components installed anywhere within the leadwire system 102 or 102' or in association with the distal tip or distal ring electrodes 120, 120' or 122, 122'.

The presence of diodes or other types of transient voltage devices internal to the AIMD 100C tend to increase the currents in implanted leads such as current $I_W$ during an AED event. The reason for this is that when a high voltage event is presented to the input of the AIMD, its circuit diodes clamp and tend to look like a very low impedance. Accordingly, there is an approximate short circuit in this situation between the leads 102 or 102' and the case or housing 124 of the AIMD. This makes for a relatively low impedance current loop which must return through body tissue. Accordingly, this sets up a worst-case event for the flow of surge currents in implanted leads.

FIG. 4 also shows an optional switch arrangement 126 and 126' which is internal to the housing 124 of the AIMD 100C. These fast acting electronic switches would be in series with the internal electronics 128 of the AIMD. In this way, during an external defibrillation event, these switches 126, 126' would rapidly and momentarily open until the high voltage pulse from the AED had dissipated. The switches 126, 126' would then reclose so that the AIMD, such as a cardiac pacemaker, could resume its normal pacing and sensing functions. By having these switches 126, 126' open up during the external defibrillation event, the impedance of the leadwire loop is raised significantly. This acts as a current limiter, not only to the internal sensitive electronic circuits 128 of the AIMD, but also would automatically limit the current that would flow in an implanted leadwire, such as the leads 102 and 102'.

Throughout the description of the invention, functionally equivalent components are usually assigned the same reference number, irrespective of the particular embodiment being described.

Figure 5:
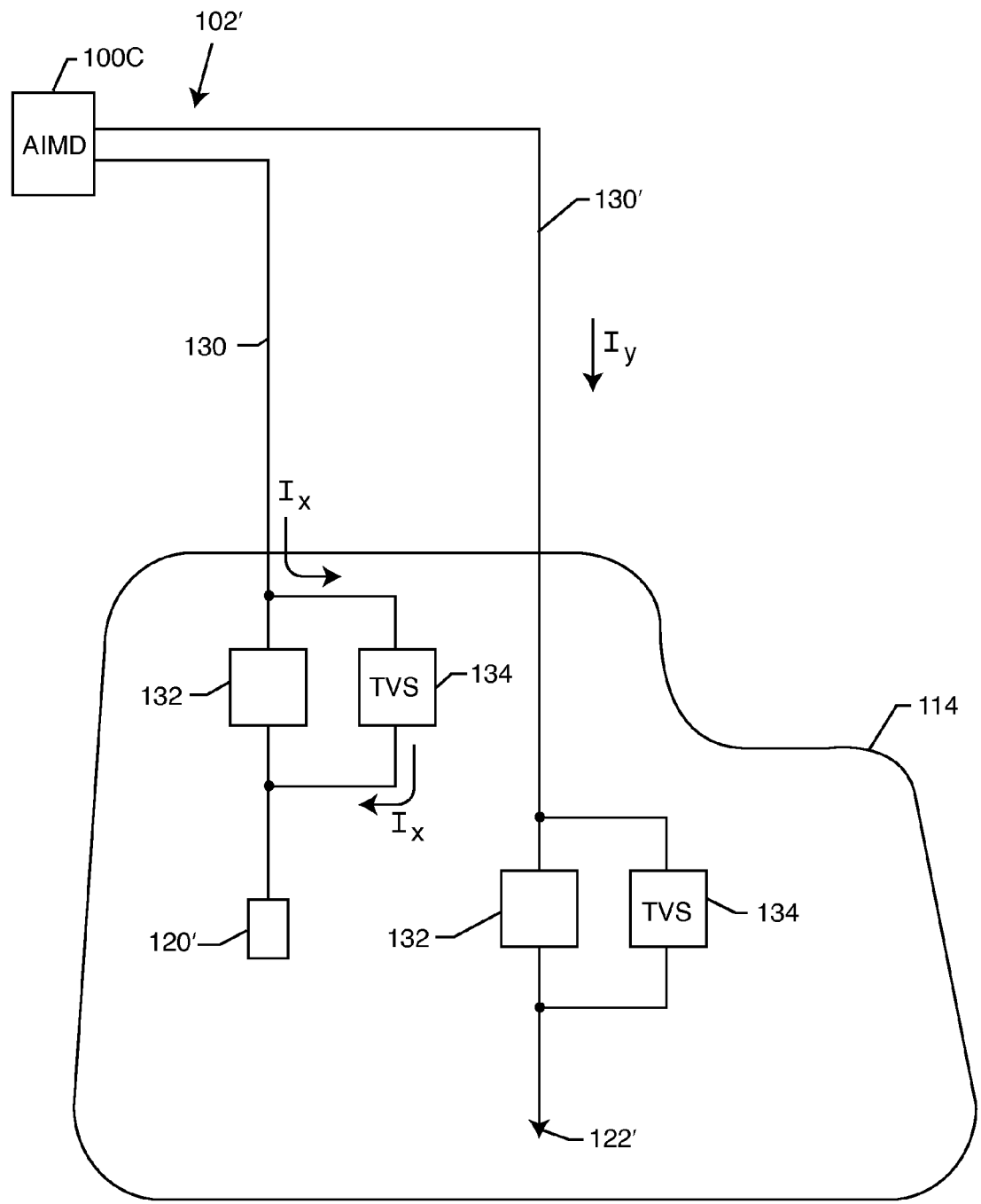
FIG. 5 is a schematic illustration similar to FIG. 4, illustrating an implanted AIMD modified to a single chamber bipolar lead system.

FIG. 5 is similar to FIG. 4 in that there is an implanted AIMD, such as a cardiac pacemaker 100C, but it has been modified to show the present invention in a single chamber bipolar lead system wherein both the ring electrode 120' and the tip electrode 122' are in the right ventricle 114. FIG. 5 shows only a blow up of lead 102'. Implanted leadwires can typically be of a bifiler or a coaxial nature. In either event, there are two leadwires 130 and 130' leading into the right ventricle 114, one feeding the tip electrode 122' which makes contact with myocardial tissue, and another feeding the ring electrode 120', which floats in the blood pool. In this case, there are electronic components or an electronic circuit 132 placed in the leadwires 130 and 130' which consist of electronic or passive filter or electronic switch elements. During an external defibrillation event, in a worst-case, excess currents flowing in the lead 102' could overheat or even burn out or fuse the components of the electronic circuits 132. In accordance with the present invention, a transient voltage suppressor (TVS) 134 has been electrically connected in parallel with the electronic circuit 132. In the case where a high voltage or high current were to build up in the leadwires 130, 130', such as current $I_X$ or $I_Y$, then the transient voltage suppressor 134 would look like a short (or a very low impedance) thereby diverting the bulk of this externally induced defibrillation current around the sensitive electronic circuit or passive filter components 132. In this way, the transient voltage suppressor or suppression circuit 134 effectively protects the lead-based electronic circuit 132 from current damage that could be caused by application of an AED.

Referring once again to FIG. 5, the AIMD could also be an ICD 100I. By design, the ICD will deliver a high voltage monophasic or biphasic waveform. This is required to defibrillate a heart which is undergoing a dangerous arrhythmia, such as ventricular fibrillation. If the leadwire system of FIG. 5 embodies a bandstop filter electronic circuit 132 in order to make the AIMD and its associated leads MRI compatible, then the defibrillation pulse, as illustrated in FIG. 3, would have to pass through the bandstop filter 132 in order to properly defibrillate the heart. This could be quite problematic in that, for such low frequency energy, the defibrillation current would have to pass through the inductor of the bandstop filter. By necessity, the wiring of the inductor must be very small so that it can pass through the venous system of the heart. Accordingly, it is not capable of handling extremely high currents such as those that would be produced by an ICD. ICD currents can, for short periods of time, exceed 10 or 25 amperes. Accordingly, it is a feature of the present invention that the transient voltage suppressor 134 protection circuits be used to bypass lead based electronic circuits during internal ICD high voltage shocks as well as bypass extraneous shocks from AEDs. Preferably, the transient voltage suppressor 134 protection circuit be of fast-acting diodes or the like so that an ICD defibrillation pulse waveform is not distorted.

FIG. 6 is a line drawing representation of a unipolar AIMD system 100. It consists of a generally hermetically enclosed housing 124 in which electronic circuits for tissue stimulation and/or sensing are housed. A unipolar lead 102 is shown connected to a distal electrode 136.

FIG. 7 illustrates a very similar system, but in this case, is bipolar. In this case, there are a pair of leadwires 130 and 130' which connect to a pair of distal electrodes 136 and 136'.

FIG. 8 is an illustration of a bipolar cardiac pacemaker 100C wherein the distal electrodes consist of a ring 120' which floats in the blood pool and a distal tip active electrode 122'. In the prior art, the distal electrode tip 122' is either a passive tip or an active fixation tip. The active fixation tip would employ a screw-type helix for affixing said distal electrode tip into myocardial tissue.

FIG. 9 illustrates a bandstop filter 138 which is designed to be placed either adjacent to the distal ring electrode 120' or the distal tip electrode 122' of FIG. 8. The bandstop filter 138, which is one type of the electric circuit 132 described previously, consists of parallel inductor 140 and capacitor 142 elements. At resonance, the bandstop filter 138 tends to form a very high impedance. This is more fully described in U.S. Pat. No. 7,373,090. Further description of bandstop filters for attenuating currents in an AIMD patient that is exposed to magnetic resonance imaging are described by in U.S. Patent Publication No. US 2007-0112398 A1; U.S. Patent Publication No. US 2008-0071313 A1; U.S. Patent Publication No. US 2008-0049376 A1; U.S. Patent Publication No. US 2008-0161886 A1; U.S. Patent Publication No. US 2008-0132987 A1; U.S. Patent Publication No. US 2008-0116997 A1; and U.S. Patent Application No. 61/016,364, the contents of all of which all are incorporated herein.

In FIG. 9 one can see that during an internal ICD or external AED high voltage shock event, high currents could flow through the inductor element 140. Such high currents flowing through an inductor element could also result in a high voltage appearing across the capacitor element 142. The rate of change in current in an inductor L causes a voltage V which is given by the equation $V_L=L(di/dt)$. A transient voltage suppressor 134 of the present invention comprises parallel back-to-back fast-acting zener diodes 144 and 144' in parallel with the bandstop filter 138 elements. In this case, if a transient voltage and resultant surge current was detected, either zener diode 144 or 144' would forward conduct and thereby both suppress the voltage and bypass the bulk of the current around the electronic circuit 132, 138. This would tend to protect both the inductor element 140 and the capacitor element 142 of the bandstop filter 138. This inventive concept is also applicable to a variety of electronic circuits including switches and lead-based sensors, in addition to the illustrated bandstop filter 138.

FIG. 10 illustrates a prior art bipolar pacemaker 100C system illustrating coaxial leadwires 130 and 130' which terminate in a distal ring 120 and distal tip 122. As previously mentioned, the distal tip 122 is either affixed or is in intimate contact with myocardial or epicardial tissue.

FIG. 11 is an enlarged schematic taken generally of the area indicated by line 11-11 from FIG. 10, and illustrates the presence of a bandstop filter 138 in series with the distal tip electrode 122 and the distal ring electrode 120 in order to provide a high impedance at a selected frequency, such as the RF pulsed frequency of a particular MRI system. For example, for 1.5 Tesla MRI, the parallel inductor L and capacitor C would be designed to resonate at 64 MHz. Also shown in parallel with the bandstop filter elements L and C is a transient voltage suppressor (TVS) 134. The transient voltage suppressor 134 could consist of back-to-back zener diodes as previously described in connection with FIG. 9, or it could consist of varistor material, or other types of transient voltage suppressors.

FIGS. 12 through 21 illustrate a family of frequency selective passive electronic circuits 132 which can be used either as high frequency diverters or high frequency impeding elements.

FIG. 12 is a diagrammatic view of a typical prior art device 146 such as a probe or catheter. There are two leadwires 130 and 130' which thread through the center of the illustrative probe or catheter 146 and terminate respectively in a corresponding pair of distal conductive electrode rings 148 and 150. Leadwires 130 and 130' are electrically insulated from each other and also electrically insulated from any metallic structures located within the catheter body. There can be any number of leads in actual probes and catheters. The overall catheter body is generally flexible and is made of biocompatible materials, which also have specific thermal properties. In addition to flexibility, probes and catheters 146 are typically steerable. It is well known that a push-pull wire (not shown in FIG. 12) can be run down the center of the catheter or probe in a lumen and then be attached to a catheter handle or pistol grip or other device so that the physician can carefully steer or thread the probe or catheter through the torturous path of the venous system, even into the ventricles of the heart. Such probes and catheters, for example, can be used for electrical mapping inside of a heart chamber, or for application of RF energy for ablation, which is used to treat certain cardiac arrhythmias. Probes and catheters have wide application to a variety of other medical applications. There are also combined catheters that can do electrical mapping and can also perform RF ablation. When the physician finds the area of arrhythmic electrical activity and wishes to ablate, he activates a switch which applies RF energy to the tip of the catheter (see, e.g., FIG. 39, which will be discussed in more detail). This would involve a third electrode right at the catheter tip of FIG. 12 (not shown). It would be extremely valuable if the catheter could be guided during real-time MRI imaging. This is important because of MRI's incredible ability to image soft tissue. In addition, when one is doing deliberate ablation, for example, around a pulmonary vein, it is important that a full circle of scar tissue be formed, for example, to stop atrial fibrillation. MRI has the ability to image the scar as it is being formed (see U.S. Pat. No. 7,155,271).

FIG. 13 is a schematic illustration showing the leadwires 130 and 130' of FIG. 12, which are routed to the two distal electrodes 148 and 150.

FIG. 14 shows the electrical schematic of FIG. 13 with a general frequency selective impedance element 152 connected between leadwires 130 and 130'. The impedance element 152 can consist of a number of frequency selective elements as will be further described. In general, the first conductive leadwire 130 is electrically coupled to the first electrode 148, the second conductive leadwire 130' is electrically coupled to the second electrode 150, and the frequency dependent reactive element 152 electrically couples the first and second leadwires 130 and 130' such that high frequency energy is conducted between the first leadwire 130 and the second leadwire 130'.

Referring once again to FIG. 14, the frequency dependent reactive element 152 tends to be electrically invisible (i.e., a very high impedance) at selected frequencies. The reactive element is desirably selective such that it would not attenuate, for example, low frequency biological signals or RF ablation pulses. However, for high frequency MRI RF pulsed frequencies (such as 64 MHz), this frequency reactive element 152 would look more like a short circuit. This would have the effect of sending the energy induced into the leadwires 130 and 130' by the MRI RF field back into the catheter body itself into which the leadwires are embedded. In other words, there are both RF energy and thermal conductivity to the probe or catheter body or sheath or shield which becomes an energy dissipating surface all along the lengths of leadwires 130 and 130' such that MRI induced energy that is present in these leadwires is diverted and converted to heat into the interior and along the catheter body itself. This prevents the heat build up at the extremely sensitive locations right at the ring electrodes 148 and 150 which are in intimate and direct contact with body tissue. In addition, the amount of temperature rise is very small (just a few degrees) because of the energy being dissipated over such a relatively high surface area.

FIG. 15 shows a capacitor 142 which represents one form of the frequency dependent reactive element 152 previously described in connection with FIG. 14. In this case, the reactive element comprises a simple capacitor connected between the first conductor or leadwire 130 and the second conductor or leadwire 130' and will have a variable impedance vs. frequency. The following formula is well known in the art: $X_C = 1/(2\pi f c)$. Referring to the equation, one can see that since frequency (f) is in the denominator, as the frequency increases, the capacitive reactance in ohms decreases. With a large number in the denominator, such as the RF pulsed frequency of a 1.5 Tesla MRI system, which is 64 MHz, the capacitive reactance drops to a very low number (essentially a short circuit). By shorting the leadwires together at this one frequency, this diverts and prevents the RF energy from reaching the distal ring electrodes 148 and 150 and being undesirably dissipated as heat into body tissue. Referring once again to FIG. 14, one can see that the impedance element 152 thereby diverts the high frequency RF energy back into the leadwires 130 and 130'. By spreading this energy along the length of leadwires 130 and 130', it is converted to heat, which is dissipated into the main body of the probe, catheter or insulation sheath. In this way, the relatively large thermal mass of the probe or catheter becomes an energy dissipating surface and any temperature rise is just a few degrees C. In general, a few degrees of temperature rise is not harmful to body tissue. In order to cause permanent damage to body tissue, such as an ablation scar, it generally requires temperatures of approximately 50° C. In summary, the frequency dependent reactive element 152, which may comprise a capacitor 142 as shown in FIG. 15, forms a diversion circuit such that high frequency energy is diverted away from the distal electrodes 148 and 150 along the leadwires 130 and 130' to a point that is distant from the electrodes, at which point the energy is converted to heat.

FIG. 16 shows an even more efficient way of diverting high frequency energy away from the electrode and accomplishing the same objective. The general reactance element 152 described in connection with FIG. 14 is shown in FIG. 16 to comprise the capacitor 142 in series with an inductor 140 to form an L-C trap electronic circuit 132. There is a particular frequency ($f_r$) at which the capacitive reactance $X_C$ and the inductive reactance $X_L$ are equal and opposite and tend to cancel each other out. If there are no losses in such a system, this results in a perfect short circuit between leadwires 130 and 130' at the resonant frequency. The frequency of resonance is given by the equation $$f_r = \frac{1}{2\pi\sqrt{LC}},$$

wherein $f_r$ is the frequency of resonance in Hertz, L is the inductance in henries, and C is the capacitance in farads.

FIG. 17 illustrates any of the aforementioned frequency dependent impedance elements 152 with the addition of series frequency selective reactances 154 and 154'. The addition of series impedance further impedes or blocks the flow of high frequency MRI induced currents to the ring electrodes 148 and 150 as will be more fully described in connection with the following drawings.

FIG. 18 is the low frequency model of FIG. 14, 15 or 16. In this regard, FIG. 18 is identical to FIG. 13, in that, once again it shows the electrical leadwires 130 and 130' connected to the distal ring electrodes 148 and 150 of the probe or catheter 146. In the low frequency model, the frequency reactive impedance elements 152 disappear because at low frequency their impedances approach infinity. Of course, leads in a probe or catheter are electrically equivalent to leads used for cardiac pacemakers, implantable cardioverter defibrillators, neurostimulators and the like. For example, reference is made to U.S. Pat. No. 7,363,090, the contents of which are incorporated herein. Accordingly, any discussion related to probes or catheters apply equally to leadwires for all active implantable medical devices as described in FIG. 1, and vice versa. Referring once again to FIG. 18, this is also the low frequency model of the circuits shown in FIG. 17. At low frequency, the frequency selective or reactive component 152 tends to look like a very high or infinite impedance. The series reactive or frequency variable elements 154 at low frequency tend to look like a very low impedance or short circuit. Accordingly, they all tend to disappear as shown in FIG. 18.

FIG. 19 is a high frequency model that illustrates how the distal electrodes or rings 148 and 150 are electrically isolated at high frequency by shorting leadwires 130 and 130' at location 156. As previously mentioned, such shorting or current diverting could be accomplished by a series resonant L-C trap circuit. FIG. 19 also shows the electrodes 148 and 150 as cut or disconnected and electrically isolated from the rest of the circuit. This is because at very high frequency series selective frequency (reactive) elements 154 tend to look like a very high impedance or an open circuit. In summary, by reactive elements 152 and 154 acting cooperatively, reactive element 152 diverts the high frequency energy while at the same time reactive elements 154 impede the high frequency RF energy. Accordingly, in the ideal case, the equivalent circuit of FIG.

19 is achieved. The high frequency MRI RF energy cannot reach the distal ring electrodes 148, 150 and cause undesirable heating at that critical tissue interface location.

FIG. 20 shows any of the previously described diverting frequency selective elements 152 in combination with series reactance components 154' shown in the form of a pair of inductors. It is well known to electrical engineers that the inductive reactance in ohms is given by the equation $X_L=2\pi fL$. In this case the frequency term (f) is in the numerator. Accordingly, as the frequency increases, the reactance (ohms) of the inductors also increases. When the frequency is very high (such as 64 MHz) then the reactance in ohms becomes extremely high (ideally approaches infinity and cuts off the electrodes). By having a short circuit or very low impedance between the leadwires 130 and 130' and then, at the same time, having a very high impedance in series with the electrodes from inductors 154', this provides a very high degree of attenuation to MRI RF pulsed frequencies thereby preventing such energy from reaching the distal ring electrodes 148 and 150. In FIG. 20, the line-to-line selective impedance element 152 diverts high frequency energy back into leadwires 130 and 130' while at the same time the series inductors 154' impede (or cut-off) high frequency energy. When the line-to-line element 152 is a capacitor 142 as shown in FIG. 15, then this forms what is known in the prior art as an L section low pass filter, wherein the capacitor 142 electrically cooperates with the inductors 154' (FIG. 20) to form a 2-element low pass filter. By definition, a low pass filter allows low frequencies such as biological signals to pass to and from the distal electrodes freely without attenuation while at the same time provides a high degree of attenuation to undesirable high frequency energy. FIG. 15 describes a single element low pass filter, and FIG. 20 describes a 2-element or L-section low pass filter. Moreover, any number of inductor and capacitor combinations can be used for low pass filters, including 3-element Pi or T circuits, LL, 5-element or even "n" element filters.

FIG. 21 offers an even greater performance improvement over that described in connection with FIG. 20. In FIG. 21, modified frequency selective elements 154" each incorporate a parallel resonant inductor and capacitor which is also known in the industry as a bandstop filter 138. The L-C components for each of the reactive elements 154" are carefully chosen such that each of the bandstop filters is resonant, for example, at the pulsed resonant frequency of an MRI scanner. The pulsed resonant frequency of an MR scanner is given by the Lamor equation wherein the RF pulsed frequency in megahertz is equal to 42.56 times the static field strength. For example, for a popular 1.5 Tesla scanner, the RF pulsed frequency is 64 MHz. Common MR scanners that are either in use or in development today along with their RF pulsed frequencies include: 0.5 Tesla-21 MHz; 1.5 Tesla-64 MHz; 3 Tesla-128 MHz; 4 Tesla-170 MHz; 5 Tesla-213 MHz; 7 Tesla-300 MHz; 8 Tesla-340 MHz; and 9.4 Tesla-400 MHz. When the bandstop filters 154" (138) are resonant at any one of these RF pulsed frequencies, then these elements tend to look like an open circuit which impedes the flow of RF current to distal electrodes. When compatibility with different types of MR scanners is required, for example, 1.5, 3 and 5 Tesla, then three separate bandstop filter elements in parallel may comprise the reactive elements 154 (FIG. 17). Each of these would have their L and C components carefully selected so that they would be resonant at different frequencies. For example, in the case of MR scanners operating at 1.5, 3 and 5 Tesla, the three bandstop filters would be resonant respectively at 64 MHz, at 128 MHz, and at 170 MHz. The resonant frequencies of the bandstop filter elements could be selected such that they are resonant at the operating frequency of other emitters that the patient may encounter such as diathermy and the like.

Figure 22:
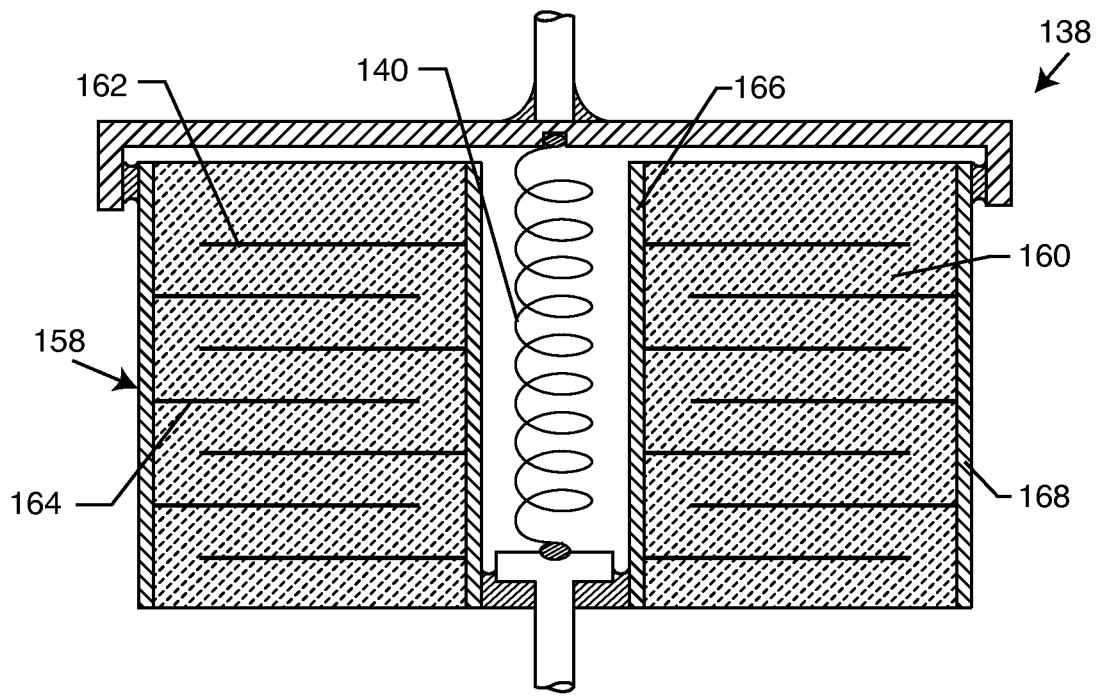
FIG. 22 is a partially fragmented sectional view of discoidal feedthrough capacitor having an inductor element to form a parallel bandstop filter circuit and utilizing a varistor dielectric material to impart TVS characteristics to the structure.

FIG. 22 illustrates a discoidal feedthrough capacitor 158 which also has an inductor element 140. This forms the parallel bandstop filter circuit 138 as shown in FIG. 9 consisting of a capacitor in parallel with an inductor. This is more thoroughly described in connection with FIG. 42 of U.S. Patent Publication No. US 2007-0112398 A1. However, there is a key difference. Instead of using typical barium titinate ceramic dielectric, the feedthrough capacitor 158 of FIG. 22 includes a varistor dielectric material 160, such as metal-oxide based ceramic. This varistor dielectric material 160 may be similar to materials used in multi-layer ZnO varistors, such as the Transguard™ voltage suppressors are available from AVX Corporation of Myrtle Beach, S.C. This is more thoroughly described in U.S. Pat. No. 5,999,398, the contents of which are herein incorporated by reference. Referring once again to FIG. 22, one can see that this is a cross-section of a typical unipolar feedthrough capacitor. There are opposed electrode plate sets 162 and 164. The active electrode plates 162 are connected to internal metallization 166 at the feedthrough hole. The ground electrode plates 164 are connected to external metallization 168. The inductor 140 is connected from one end of the capacitor 158 to the other which places the inductive element in parallel with the capacitive element, forming a bandstop filter 138. The active electrode plates 162 are separated from the ground electrode plates 164 by the varistor dielectric material 160. When low voltage is applied to the capacitor 158, the dielectric material 160 has a fairly high resistivity and a relatively high dielectric constant. Accordingly, one can tune the capacitor 158 in accordance with the principles of bandstop filters as described in U.S. 2007/0112398. However, when a high voltage appears across the varistor dielectric material 160, it tends to go to a very low impedance or short circuit. This allows it to pass very high surge currents without damage to the inductor element 140 in accordance with the present invention.

Figure 23:
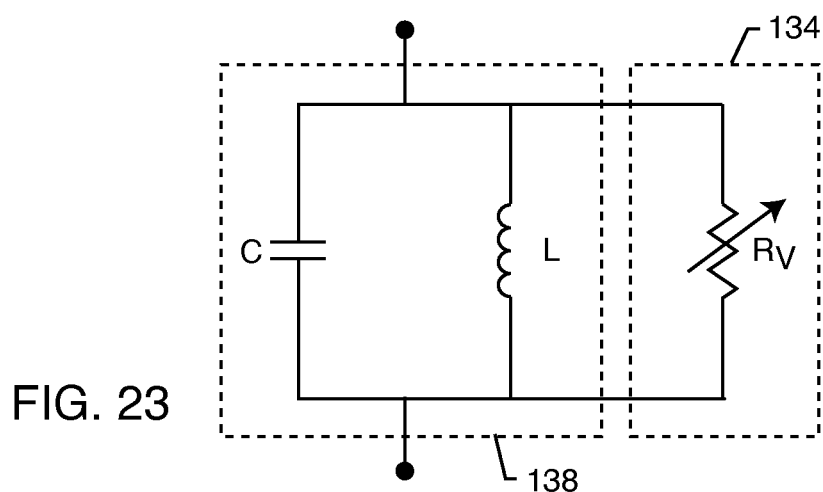
FIG. 23 is an electrical schematic illustration of the structure shown in FIG. 22.

As one can see in the schematic diagram in FIG. 23, a capacitance C is formed between the electrode plates. However, there is also a variable resistor (varistor) $R_V$ as shown. The inductor L (140) is shown in parallel with the capacitor element C. When a high voltage is present, the capacitor's varistor dielectric 160 tends to be very conductive, which acts as a transient voltage suppressor 134 in accordance with the present invention. This is an important illustration of a way in which transient voltage suppression characteristics can be integrated directly into the design of the electronic circuit 132.

Figure 24:
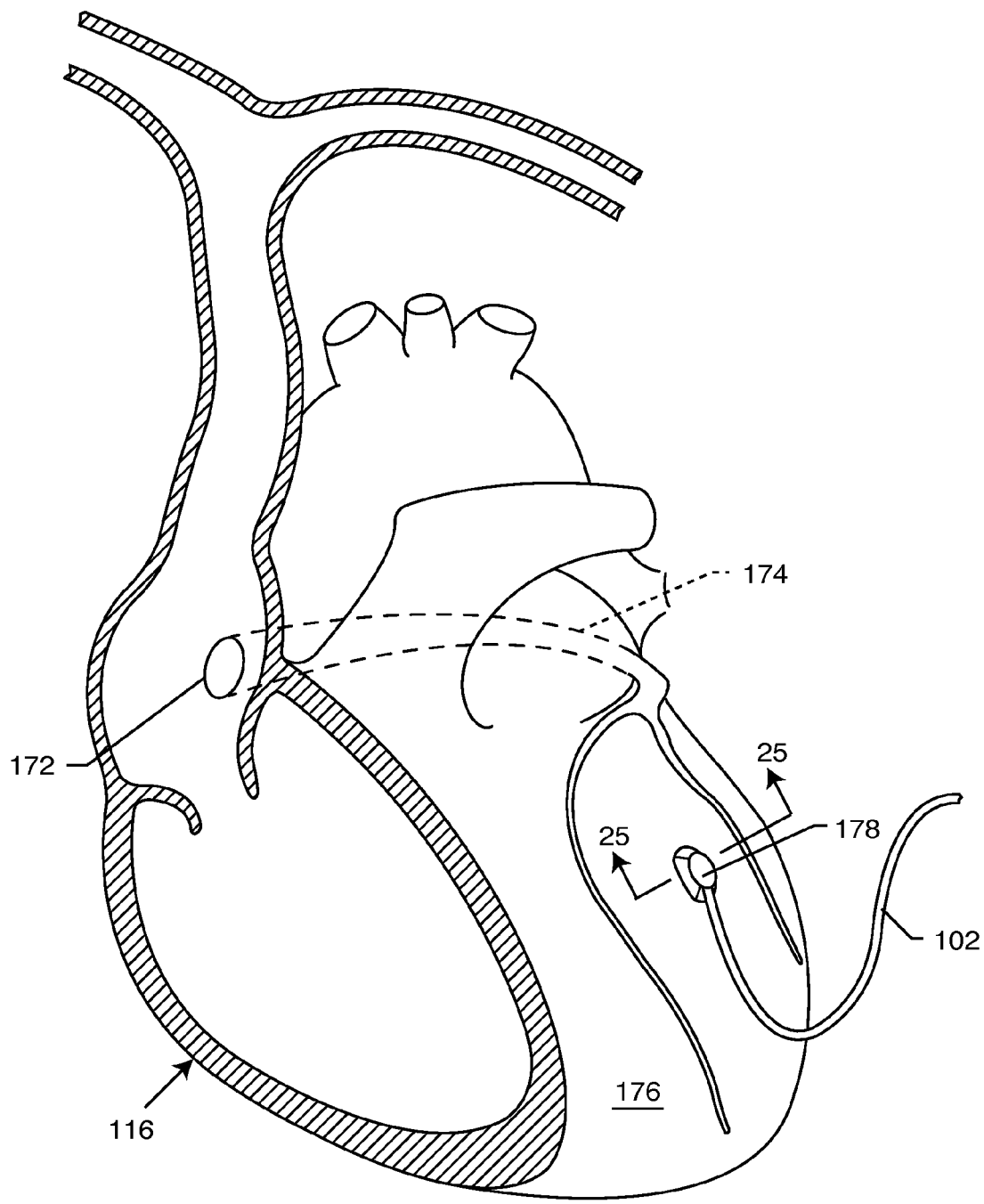
FIG. 24 is a diagrammatic representation of the human heart, showing epicardial leadwire attachment to the outside of the left ventricle.

FIG. 24 is taken from FIG. 3 of U.S. Patent Publication No. US 2008-0132987 A1. Shown is a line diagram of the heart 116 showing the coronary sinus 172 and the great cardiac vein 174. Also shown is the area outside of the left ventricle 176. Shown is an epicardial lead 102 that is connected to a sutureless or sutured distal tip epicardial bipolar electrode 178.

Figure 25:
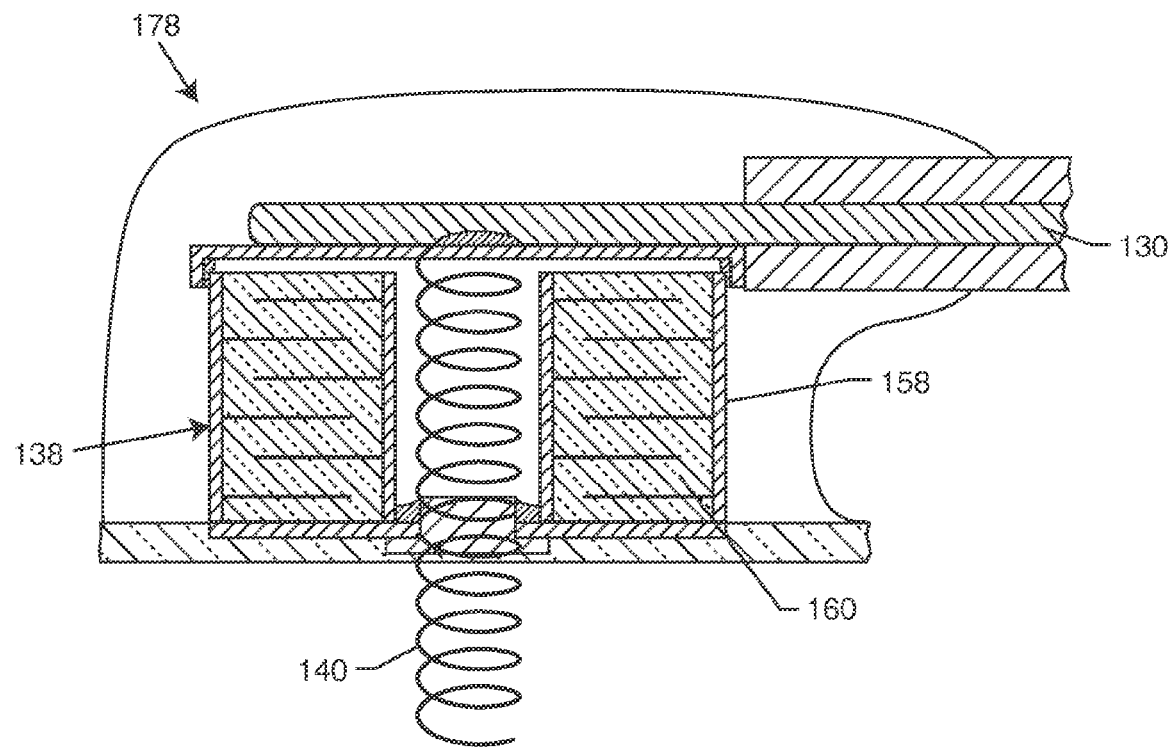
FIG. 25 is a cross-sectional view of an epicardial lead embodying a bandstop filter.

FIG. 25 is a sectional view along line 25-25 from FIG. 24 and shows a novel bandstop filter 138 arrangement incorporating the novel feedthrough capacitor 158 and parallel inductor 140 of FIG. 22. Also incorporated are the transient voltage suppressor formed by using varistor dielectrics 160.

Figure 26:
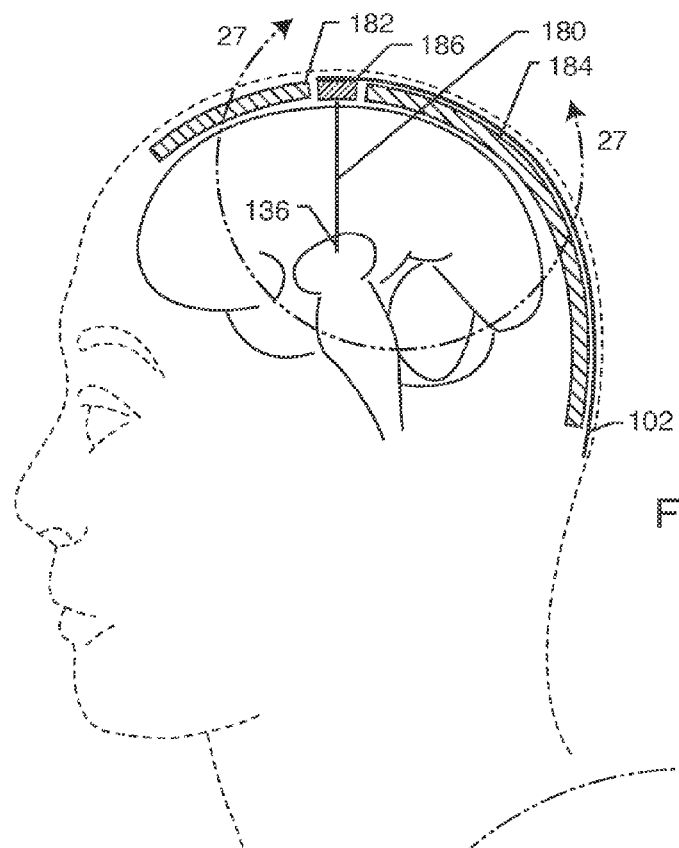
FIG. 26 is a diagrammatic, side cross-sectional view of the human head showing the placement of a deep brain probe and electrode.
Figure 27:
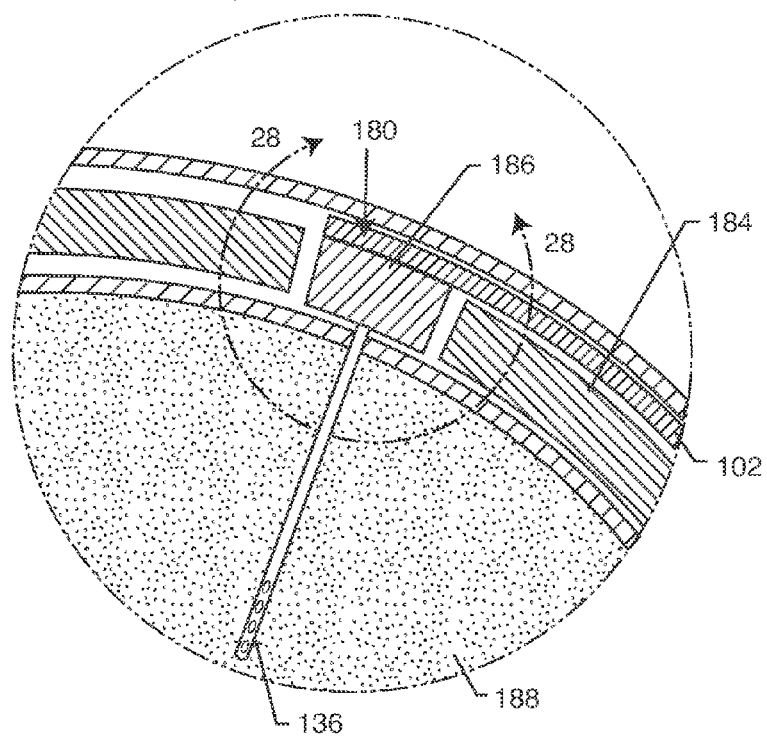
FIG. 27 is an enlarged sectional view of the area designated by line 27-27 in FIG. 26.

FIGS. 26 and 27 are taken from FIGS. 13 and 14 of U.S. Patent Publication No. US 2008-0132987 A1. Referring to FIG. 26, one can see an outline of the human head showing a deep brain electrode 180 that is placed in a burr hole 182 drilled in the skull 184. The distal electrodes 136 are placed precisely in brain tissue so that they can perform the correct neurostimulation or neuromodulation function. Leads 102 are routed up the back of the neck and are connected to the deep brain electrode(s) 180. The lead 102 is routed down typically into the pectoral region of the chest where an AIMD may be implanted (not shown).

FIG. 27 is an enlarged view of the area indicated by the line 27-27 from FIG. 26. One can see that the deep brain electrode (s) 180 consists of a leadwire bundle 102 which is connected to a generally encapsulated or hermetically sealed electronics module 186. The electronics module 186 can be placed within the skull 184 or subdural (not shown). The distal electrodes 136 are implanted deeply into brain tissue 188.

Figure 28:
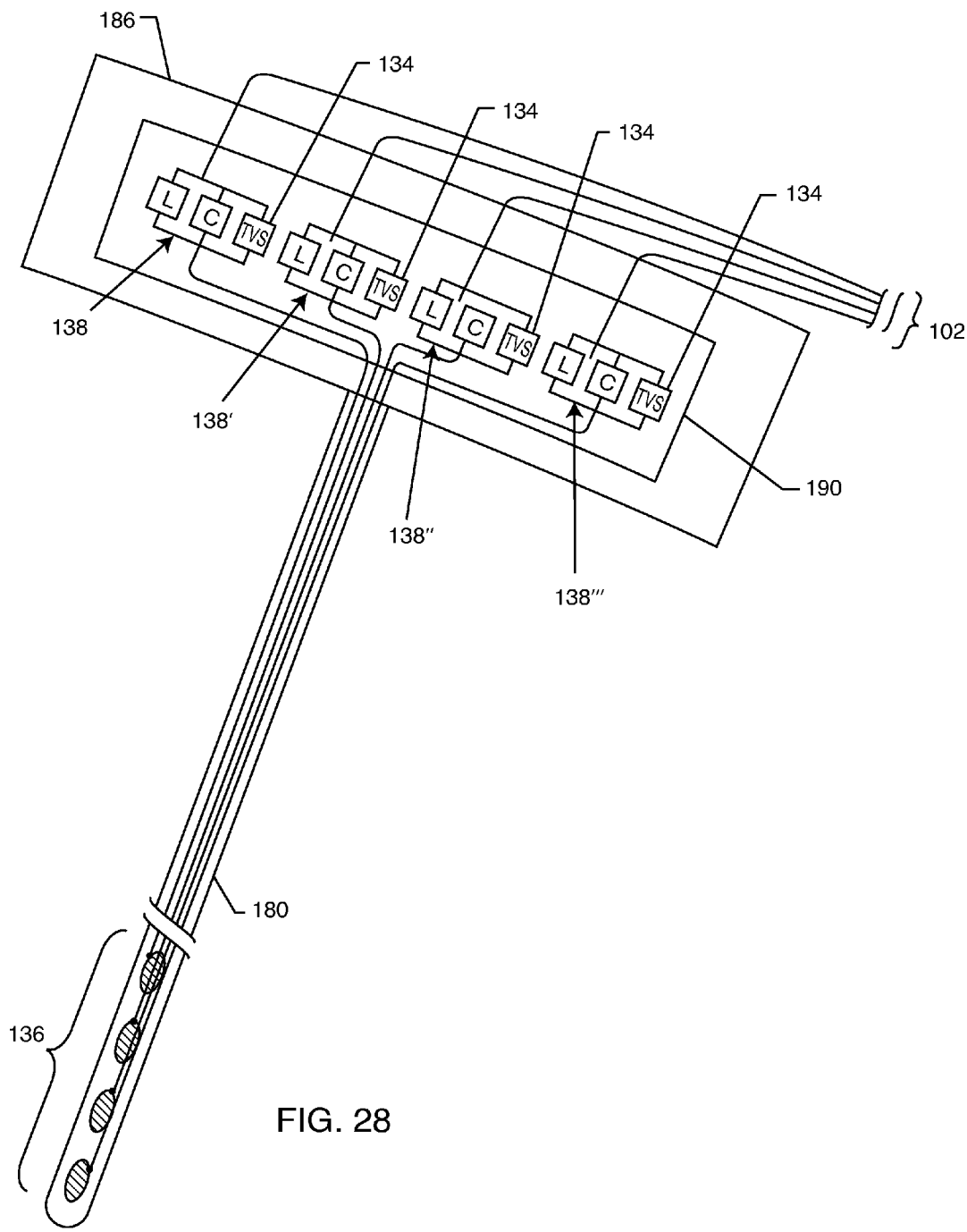
FIG. 28 is an enlarged view taken of the area indicated by line 28-28 in FIG. 27, illustrating use of transient voltage suppressors in parallel with electronic circuits in series with each electrode leadwire.

FIG. 28 is a schematic illustration of the wiring and electronic components within the area indicated by line 28-28 of FIG. 27. Shown is an electronic circuit board 190 which is embedded within the electronics module 186. In this case, there are four bandstop filters 138-138''' consisting of an inductor L in parallel with a capacitor C. Also shown is a transient voltage suppressor TVS 134 which is in parallel with each one of the bandstop filter circuits 138-138'''. This provides protection against transient voltage events. In this case, AED paddles would not be placed, obviously, on the human head. However, as previously mentioned, the AIMD for the deep brain stimulator could be implanted in the pectoral region of a patient's chest. Accordingly, the implanted leads could pick up transient voltages or high current surges. Therefore protection of the deep brain stimulator electronics module 186 from high voltage transients is equally important as it would be for cardiac a pacemaker. This is particularly important if the inductor and capacitor resonator elements were of delicate MEMS type structures.

Figure 29:
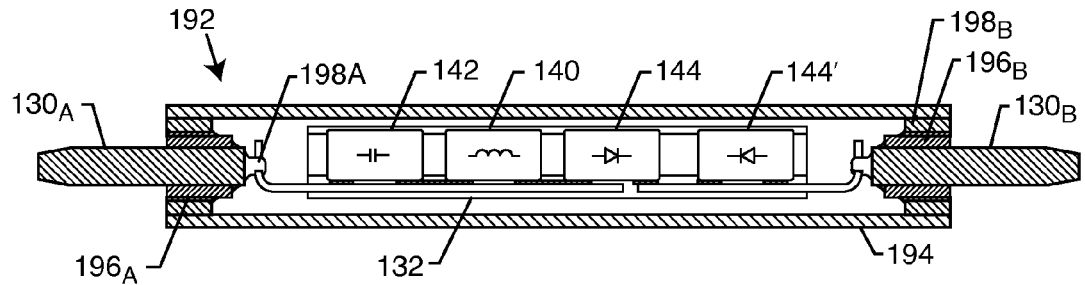
FIG. 29 is a sectional drawing of a hermetic terminal suitable for incorporation of a transient voltage suppressed bandstop filter of the present invention.

FIG. 29 is a sectional drawing of a hermetic terminal 192 suitable for incorporation of the novel transient voltage suppressed bandstop filter of the present invention. There are leadwires $130_A$ and $130_B$ that enter in and exit the hermetic housing 194. In general, the housing 194 would be of a suitable biocompatible material such as a ceramic, titanium or other precious metal. Insulators $196_A$ and $196_B$ are shown which provide a hermetic seal between the hermetic housing 194 and the leadwires $130_A$ and $130_B$. Hermetic insulator $196_A$ and $196_B$ can be installed either by gold brazed preforms or by prior art compression or fusion glass sealing techniques. There are internal electrical connections at points $198_A$ and $198_B$ for connecting the flex electronic circuit 132 (within the hermetic package) to leadwires $130_A$ and $130_B$.

Figure 30:
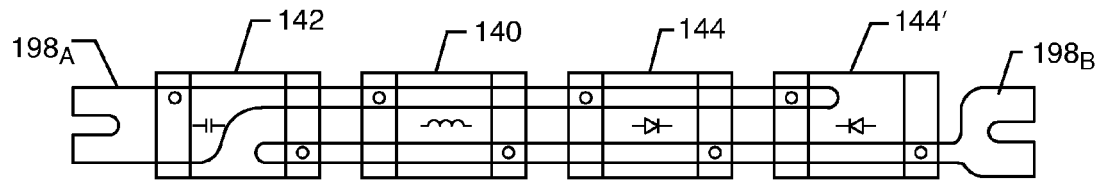
FIG. 30 is a detailed internal component layout wiring diagram of the flex electronic circuit of FIG. 29.
Figure 31:
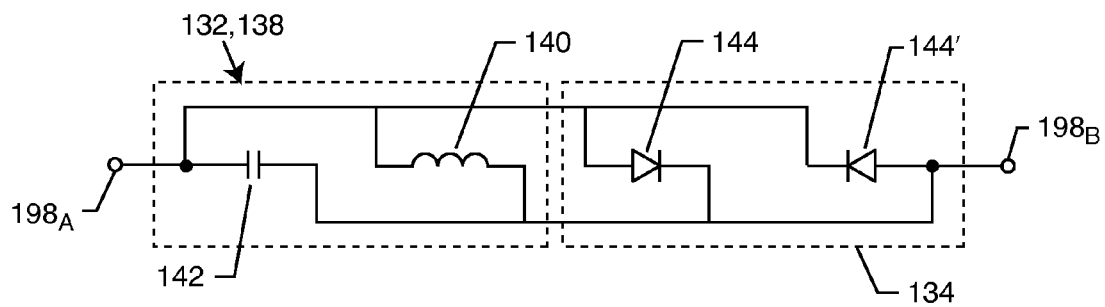
FIG. 31 is an elongated electrical schematic of the flex electronic circuit of FIGS. 29 and 30.
Figure 32:
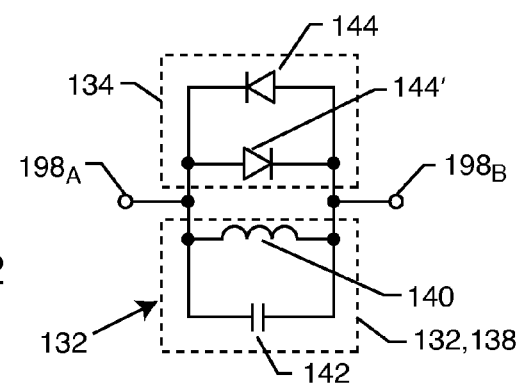
FIG. 32 is an equivalent electrical schematic of that shown in FIG. 31.

FIG. 30 is a detailed internal component layout wiring diagram of the flex electronic circuit 132 of FIG. 29. If one follows the circuit traces carefully, one will see that the capacitor 142 and the inductor 140 are wired in parallel along with diodes 144 and 144'. This is better understood by referring to FIG. 31 which is a schematic of the flex electronic circuit 132 of FIGS. 29 and 30. The equivalent electrical schematic of FIG. 31 is shown in FIG. 32. FIGS. 31 and 32 make it clear that the inductor 140, the capacitor 142, and the diodes 144 and 144' are all in parallel. This forms a bandstop filter 138 with back-to-back transient voltage protection diodes (134) in accordance with the present invention.

Figure 33:
FIG. 33 is an illustration showing the hermetic package of FIG. 29 next to a U.S. penny.

FIG. 33 shows the hermetic package 192 of FIG. 29 next to a U.S. penny. One can see how small the hermetic package 192 really is.

Figure 34:
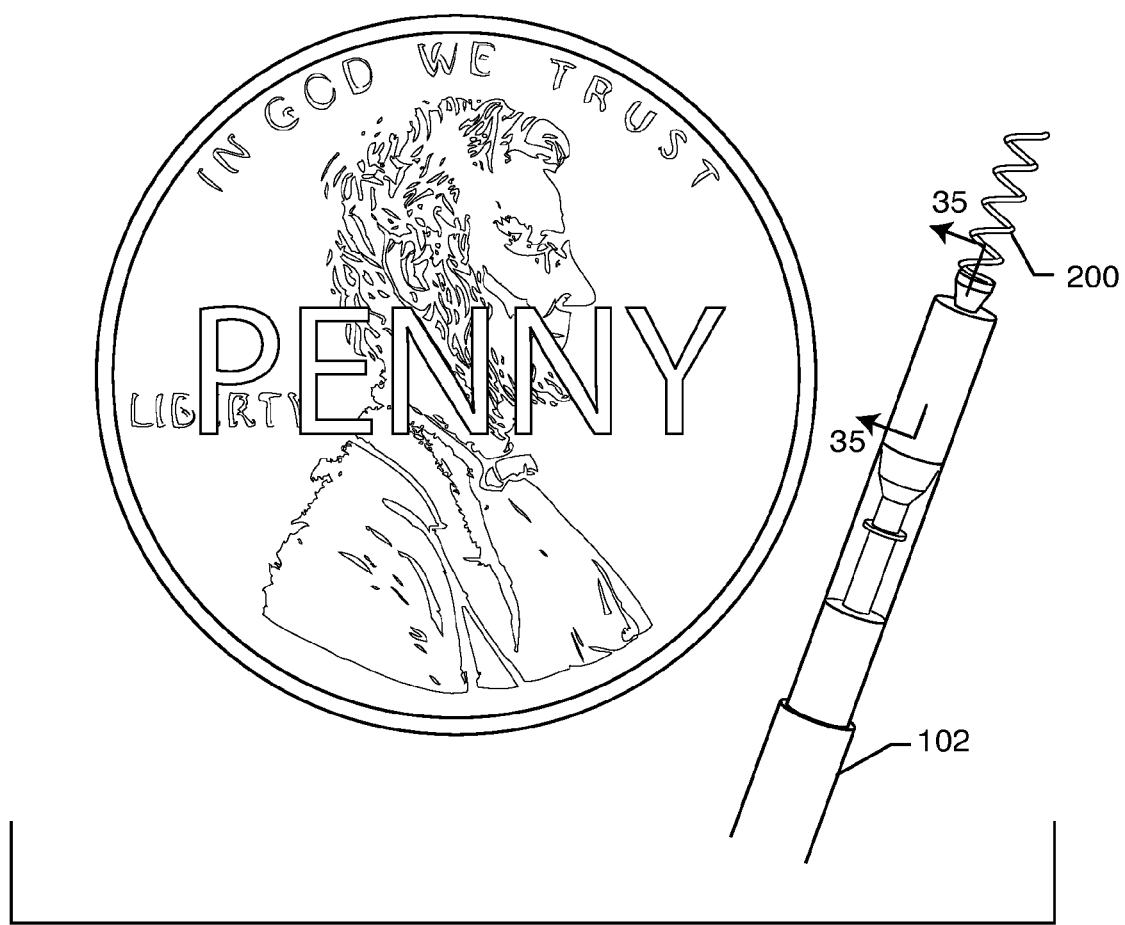
FIG. 34 is an illustration similar to FIG. 33, illustrating an active fixation tip of an implanted lead that is typical of a cardiac pacemaker.
Figure 35:
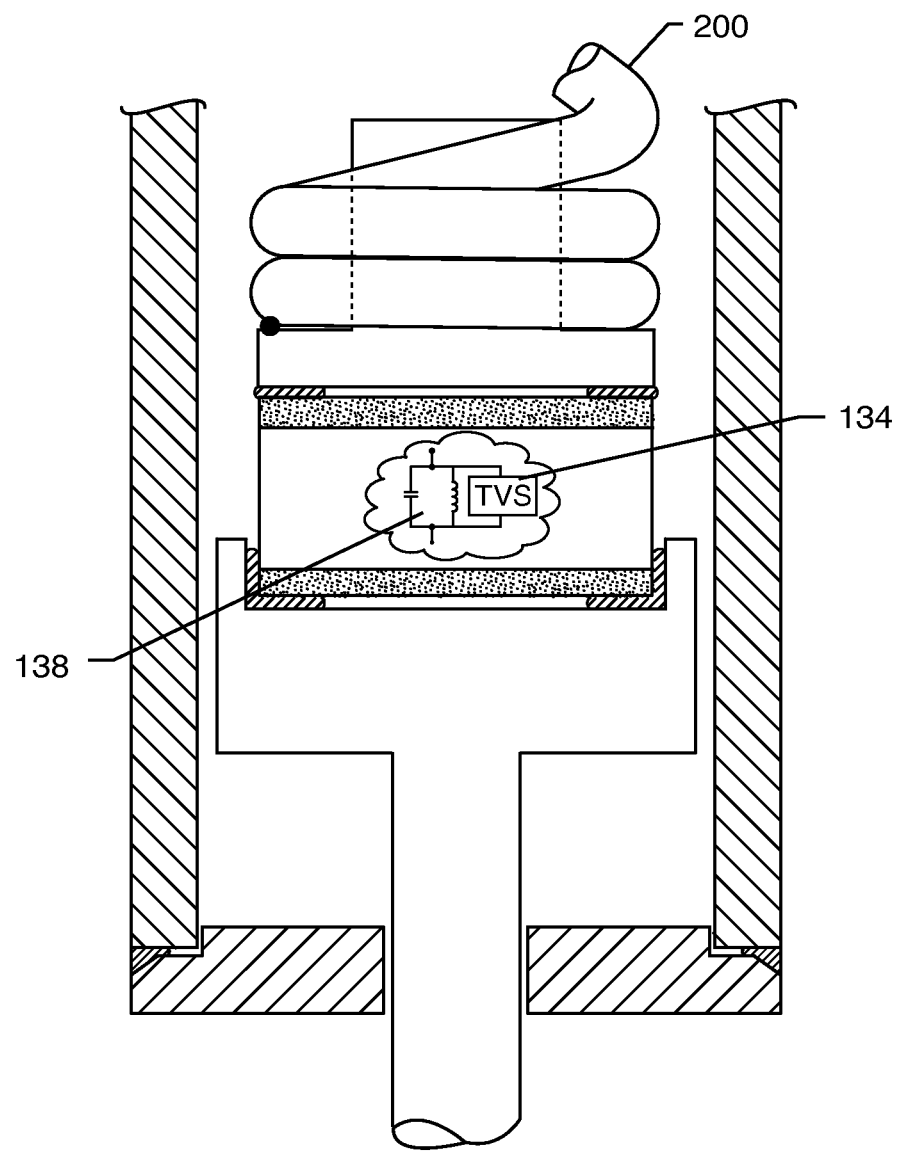
FIG. 35 is a sectional view of a cardiac active fixation tip electrode.

FIG. 34 illustrates an active fixation tip 200 of an implanted lead 102 that is typical of a cardiac pacemaker. The electrode helix tip 200 is designed to be screwed into myocardial tissue. This is also shown in relation to a U.S. penny. The active fixation tip 200 may also incorporate the novel hermetically sealed bandstop filter 138 and parallel transient voltage suppressor 134 in accordance with the present invention. This is more clearly illustrated in FIG. 35, which is a sectional view taken from line 35-35 of FIG. 34 of the active electrode fixation tip 200. One can see the helix tip 200, which is attached to the bandstop filter assembly 138, consists of a parallel inductor and capacitor along with a transient voltage suppressor 134 of the present invention. This makes the lead system not only MRI compatible, but also compatible with either internal high voltage shocks from an ICD or external high voltage shocks from an AED.

Figure 36:
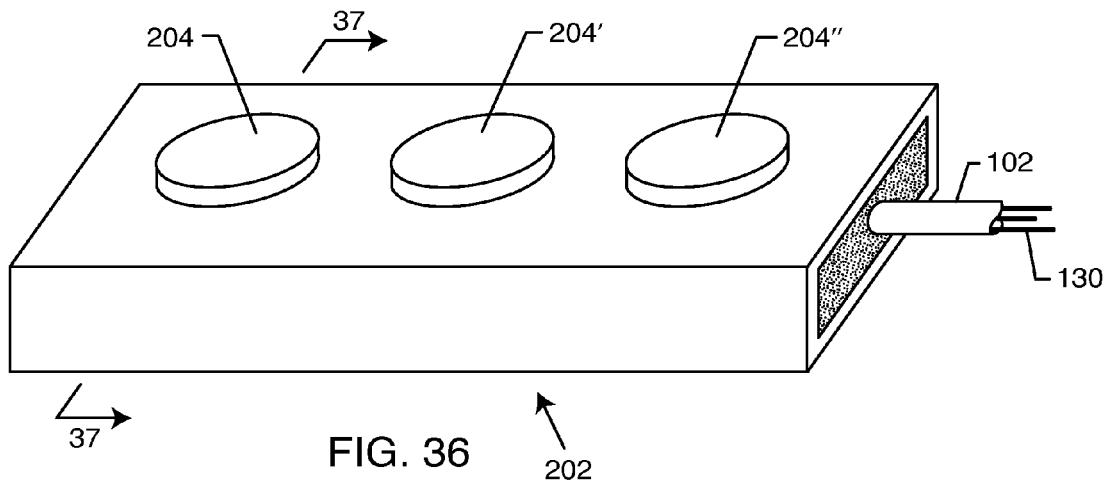
FIG. 36 is a perspective view of a distal electrode pad applicable to a wide variety of neurostimulator and neuromodulator applications.

FIG. 36 is taken from FIG. 22 of U.S. Patent Application No. 61/016,364. Shown is a neurostimulation electrode assembly 202 that would be typically used in a spinal cord stimulator or other type of neurostimulator application. Shown are three electrodes 204, 204' and 204". A leadwire bundle 102 from the AIMD is also shown.

Figure 37:
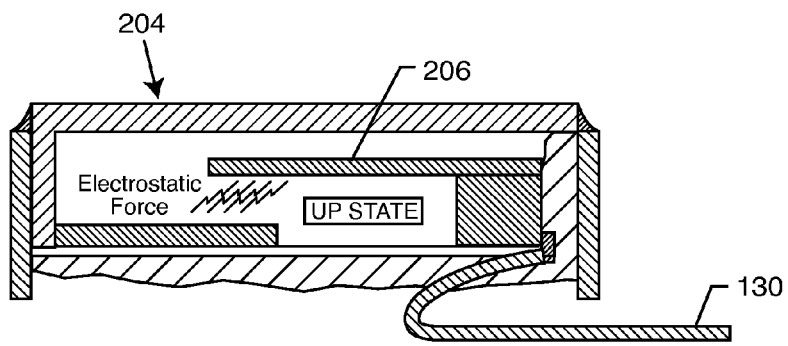
FIG. 37 is a sectional view taken along line 37-37 from FIG. 36, illustrating a MEMS switch in the up-state or open position.
Figure 38:
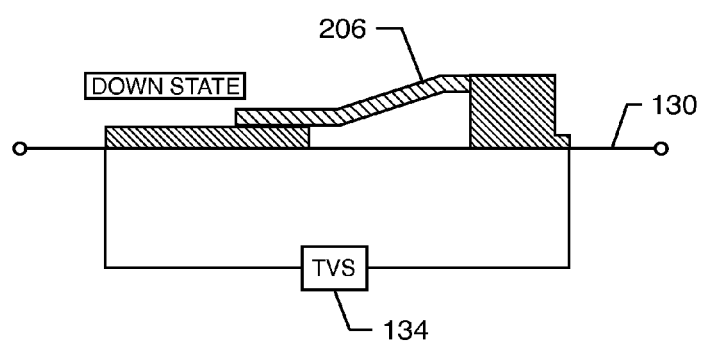
FIG. 38 is a schematic illustration of the structure shown in FIG. 37, illustrating application of an electrostatic force to cause the MEMS switch to close into a down-state.

FIG. 37 is an enlarged section taken underneath the electrode pad 204 taken from FIG. 36 (204' and 204" are similar). Shown is a MEMS switch 206 in the up state or open position. Application of an electrostatic force causes the MEMS switch 206 to close into the down state as illustrated in FIG. 38. Also shown in FIG. 38 is a transient voltage suppressor 134 of the present invention which would be in parallel with the MEMS switch 206. This would protect the relatively sensitive MEMS device from transient voltage/surge current events such as those from AEDs.

Referring once again to FIGS. 36, 37 and 38, one should understand that the MEMS switch 206 is a very delicate electronic switch which is used to make the neurostimulation electrodes 466 204-204" safe during MRI procedures. During an MRI, the MEMs switch would open and these electrodes would be disconnected from the associated elongated leadwires 130 which run to the AIMD (not shown). In normal operation, the MEMs switches are closed. Stimulation currents, for example, those for a spinal cord stimulator, are only a few micro-amps or milliamperes. Accordingly, the MEMS switch 206 can be made of very small and delicate foil-type materials. However, if the patient were to receive emergency defibrillation from an AED, excessive currents could cause the MEMS switch 206 to literally burn-up or fuse open. As shown in FIG. 38, the presence of the transient voltage suppressor 134 of the present invention bypasses such defibrillation currents thereby protecting the MEMS switch 206 from burning out. This is particularly important when it's in its normal closed state or down state (delivering therapy).

Figure 39:
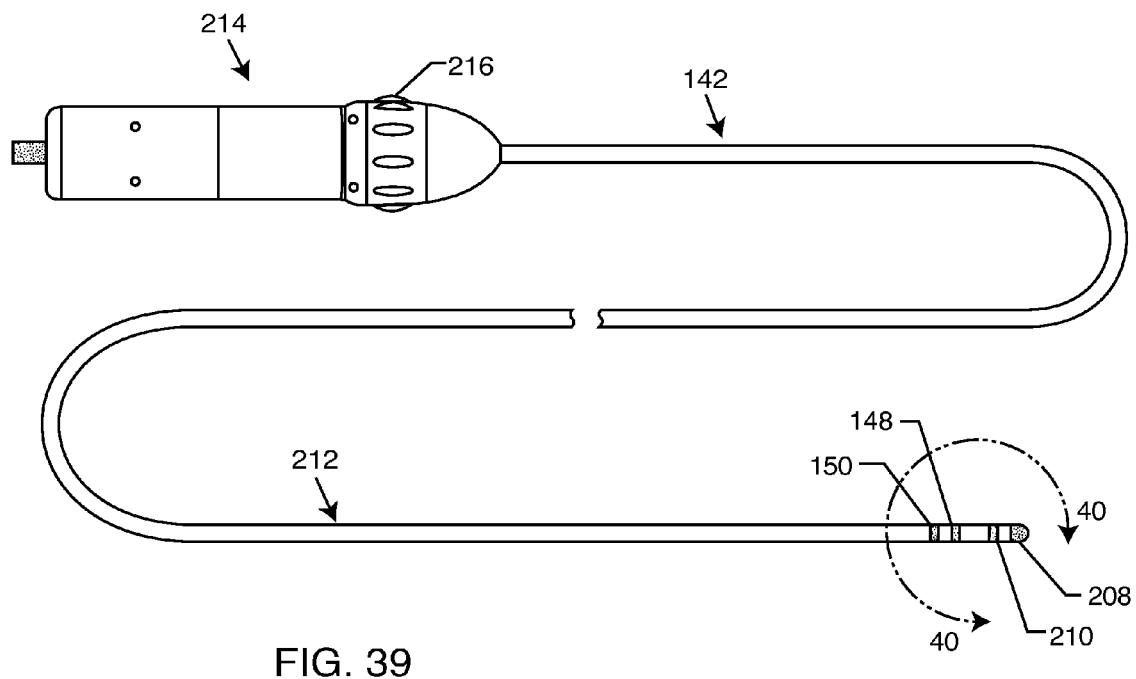
FIG. 39 illustrates a steerable catheter.

FIG. 39 shows a steerable catheter 142, which is typically used for a variety of applications including RF or cryo-ablation, cardiac mapping and many other purposes. Examples of RF ablation include treatment for atrial fibrillation, nephrotic conditions, liver, brain, cancers and the like. This would enable stereotactic ablation of certain lesions within the lung. An emerging field is the entire field of using ablation to treat various ventricular arrhythmias, including ventricular tachycardia. The illustrated catheter 142 is meant to be representative of all types of catheters or probes which can be inserted into the venous system or other areas of the human body. The catheter 142 has a tip 208 and an adjacent electrode ring surface 210, and a main catheter body 212, which can be steered around torturous paths. Also shown are a second pair of bipolar electrodes 148 and 150. These can also be used for electrical mapping, ablation or the like. The steerable catheter 142 has a handle 214 which can have various shapes, sizes and configurations. By twisting the illustrated cap 216 of the handle 214, one is able to steer the catheter 142 causing its tip 208 or other segments to bend as one guides it.

Figure 40:
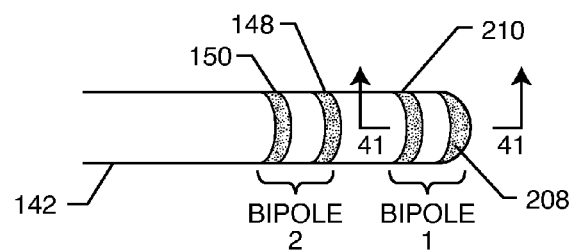
FIG. 40 is an enlarged fragmented view of a distal end of the steerable catheter of FIG. 39, taken generally of the area indicated by the line 40-40 in FIG. 39.
Figure 41:
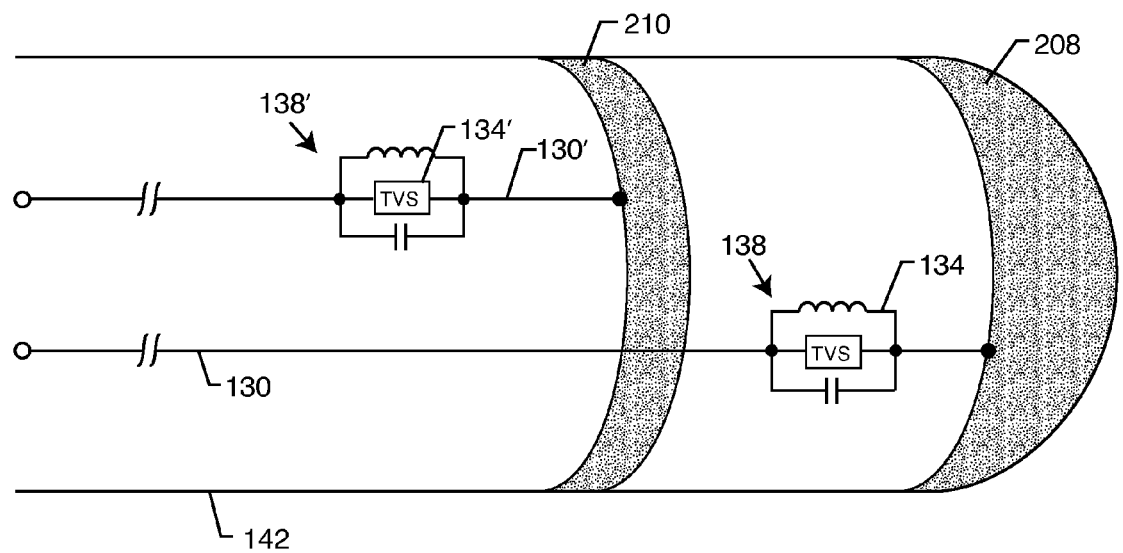
FIG. 41 is an enlarged fragmented sectional view taken generally along the line 41-41 on FIG. 40.

FIG. 40 is an enlarged view of the area indicated by line 40-40 of FIG. 39. FIG. 41 is generally taken from section 41-41 in FIG. 40 and shows internal components associated with the first bipolar electrode pair. This consists of electrode-ablation tip 208 and ring electrode 210. One can see that there are bandstop filters 138 and 138' in series with the elongated catheter leadwires 130 and 130'. Each of the bandstop filters 138, 138' is protected by a transient voltage suppressor 134 and 134'. The bandstop filters allow the probe or catheter to be MR guided without any fear of overheating of its distal electrode tip 208 or distal electrode ring 210. However, it is quite common, for example, during atrial ablation procedures, for the heart to suddenly go into a dangerous arrhythmia, such as a ventricular arrhythmia. In this case, the patient must be immediately defibrillated. The most efficient way to defibrillate such a patient is to apply a biphasic defibrillation pulse similar to FIG. 3 to the distal electrode 208. In this case, the bandstop filters 138 and 138' on the return electrode must be able to handle the full defibrillation current. The transient voltage suppressors 134 and 134' will bypass the transient voltage induced surge current past the inductor and capacitor of the bandstop filters 138 and 138', thereby allowing the defibrillation (surge) current to directly reach cardiac tissue and properly defibrillate the heart. This also prevents both the inductor (L) and capacitor (C) elements of the bandstop filters from being damaged due to excess voltage or current.

Figure 42:
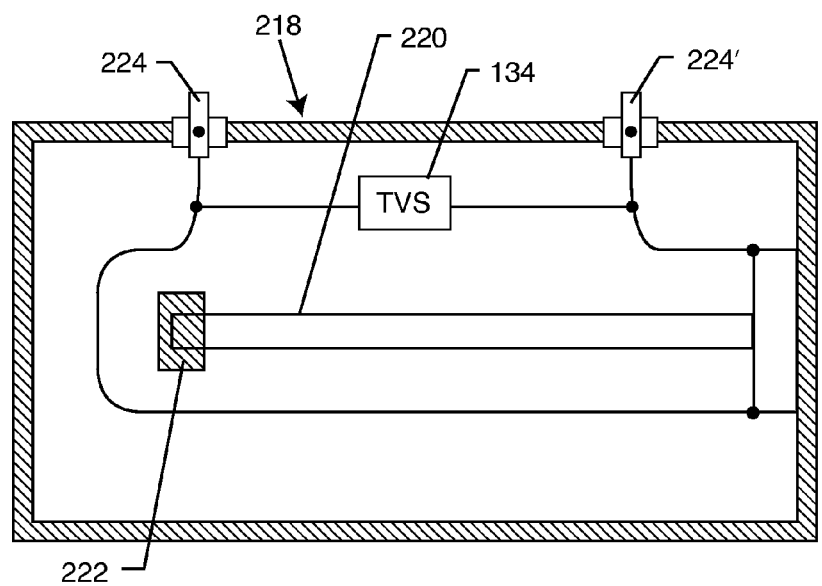
FIG. 42 is a schematic line diagram for a lead-based sensor incorporating the transient voltage suppressor of the present invention.

FIG. 42 is a line diagram illustrating a lead-based sensor 218. In this case, there is an accelerometer cantilever beam 220 that has a weight 222 on its end. The cantilever beam 220 is a piezoelectric ceramic which, when deflected, generates a small electrical signal. This electrical signal allows one to obtain cardiac rate response. For example, if the lead-based sensor 218 were affixed outside the left ventricle, the cantilever beam 220 would swing with each beat of the heart and produce a small electrical pulse. This would be connected to wiring, not shown, at connectors 224 and 224' which would be routed through the endovascular system to an AIMD, such as a cardiac pacemaker. During an AED event, very high currents could flow in this system and cause excessive surge currents to flow through the delicate piezoelectric cantilever bridge. This could burn it out and thereby take away important rate sensing information from the cardiac pacemaker. In accordance with the invention, a transient voltage suppressor 134 is wired in parallel with the cantilever beam sensor 220 such that it be protected from transient voltage surges or high current surges. FIG. 42 is only illustrative of one type of lead-based sensor. There are many in the prior art which can all be protected by transient voltage suppressors in accordance with the present invention. These include pulse oxygen sensors, blood gas analyzers, pressure transducers, other types of motion transducers and the like. Moreover, there are a number of other applications for a lead-based transient voltage suppressor/surge protector, to protect lead-based electronic circuits.

Transient voltage suppression (TVS) diodes are electronic components used to protect sensitive electronics from voltage spikes induced on connected wires. They are also commonly referred to as a transorb The device operates by shunting excess current when the induced voltage exceeds the avalanche breakdown potential. It is a clamping device, suppressing all over-voltages above its breakdown voltage. Like all clamping devices, it automatically resets when the over-voltage goes away, but absorbs much more of the transient energy internally then a similarly rated crowbar device.

Figure 43:
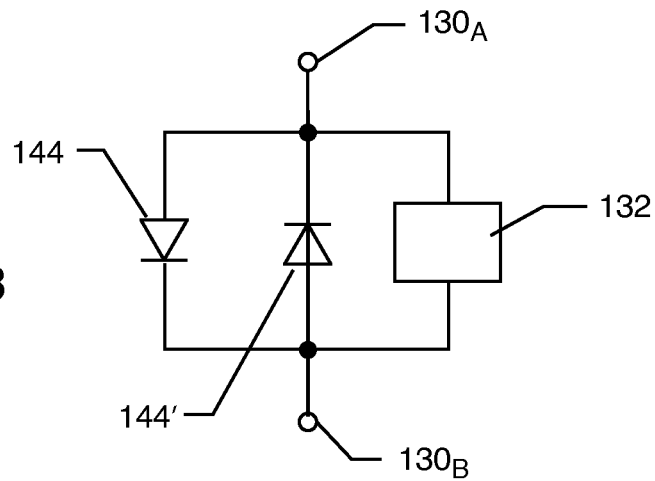
FIG. 43 is an electrical schematic showing two unidirectional transient voltage suppression diodes wired in back-to-back relation, in parallel with an implanted lead electronic circuit.

FIG. 43 shows two unidirectional transient voltage suppression diodes 144 and 144' wired in "back-to-back" configuration in parallel with an implanted lead electronic circuit 132. A transient voltage suppression diode may be either unidirectional or bidirectional. A unidirectional device operates as a rectifier in the forward direction like any other avalanche diode, but is made and tested to handle very large peak currents. (The popular 1.5 KE series allows 1500 W of peak power, for a short time.)

Figure 44:
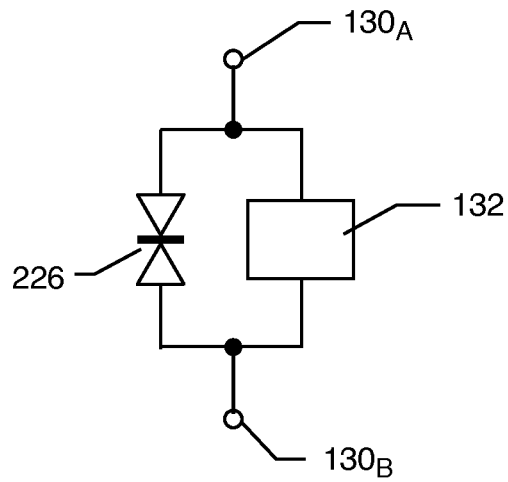
FIG. 44 is an electrical schematic similar to FIG. 43, wherein a bi-directional transient voltage suppression diode is illustrated by two mutually opposing avalanche diodes in series with one another.
Figure 45:
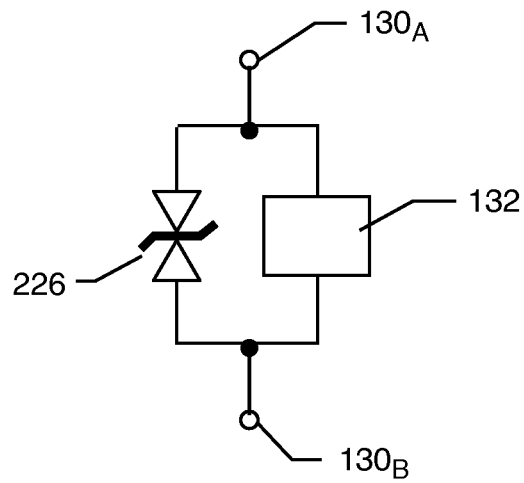
FIG. 45 is an electrical schematic illustration similar to FIG. 44, illustrating another type of bi-directional transient voltage suppression diode in parallel with the implanted lead electronic circuit, all in accordance with the present invention.

As shown in FIGS. 44 and 45 a bidirectional transient voltage suppression diode 226 can be represented by two mutually opposing avalanche diodes in series with one another and connected in parallel with the implanted lead electronic circuit 132 to be protected. While this representation is schematically accurate, physically the devices are now manufactured as a single component. Such bi-directional transient voltage suppression diodes 226 are interchangeable with and can replace any of the transient voltage diodes 144, 144' illustrated in the accompanying drawings.

A transient voltage suppression diode 144 is the preferred embodiment in all of the drawings of the present invention because it can respond to over-voltage protection components such as varistors or gas discharge tubes. The actual clamping occurs in roughly one picosecond, but in a practical circuit the inductance of the wires leading to the device imposes a higher limit. This makes transient voltage suppression diodes 144 useful for protection against very fast and often damaging voltage transients.

By way of summary, a TVS diode in characterized by:
Leakage current: the amount of current conducted when voltage applied is below the Maximum Reverse Standoff Voltage.
Maximum Reverse Standoff Voltage: the voltage below which no significant conduction occurs.
Breakdown voltage: the voltage at which some specified and significant conduction occurs.
Clamping voltage: the voltage at which the device will conduct its fully rated current (hundreds to thousands of amperes).
Parasitic capacitance: the nonconducting diode behaves like a capacitor, which can have a deleterious effect on high-speed signals. Lower capacitance is generally preferred.
Parasitic inductance: Because the actual over-voltage switching is so fast, the package inductance is the limiting factor for response speed.
Amount of energy it can absorb: Because the transients are so brief, all of the energy is initially stored internally as heat; a heat sink only affects the time to cool down afterward. Thus, a high-energy TVS must be physically large. If this capacity is too small, the over-voltage will possibly destroy the device and leave the circuit unprotected.

From the foregoing it will be appreciated that the present invention relates to a transient voltage/surge current protection system comprising (1) a lead having a proximal end and a distal end, disposed within a living body, (2) an electronic circuit associated with the lead between the proximal end and the distal end, and (3) a transient voltage suppressor electrically connected in parallel with the electronic circuit. The transient voltage suppressor advantageously provides a rapid electronic switch, which is electrically connected in parallel with the electronic circuit to momentarily close until a high voltage pulse, which creates a surge current dissipates.

Although several embodiments of the invention have been described in detail for purposes of illustration, various modifications of each may be made without departing from the spirit and scope of the invention. Accordingly, the invention is not to be limited except as by the appended claims.

We claim:
1. An implantable lead configured to be disposed within a living body, the implantable lead comprising:

a) a first, lead wire portion extending from a first lead wire portion proximal end to a first lead wire portion distal end and a second lead wire portion extending from a second lead wire portion proximal end to a second lead wire portion distal end, wherein the first lead wire portion proximal end is electrically connectable to a medical device;

b) an electronic circuit comprising a circuit first end and a circuit second end, wherein the circuit first end is electrically connected to the first lead wire portion distal end at a first node and the circuit second end is electrically connected to the second wire portion proximal end at a second node to thereby electrically connect the electronic circuit in series with the first and second lead wire portions; and c) a first transient voltage suppressor electrically connected in parallel with the electronic circuit, wherein the first transient voltage suppressor comprises:

i) a first unidirectional diode having first P and N ends and a second unidirectional diode having second P and N ends, ii) wherein the P end of the first diode is electrically connected at the first node to the N end of the second diode and to the electronic circuit first end, and iii) wherein the N end of the first diode is electrically connected at the second node to the P end of the second diode and to the electronic circuit second end to thereby provide the first and second diodes in parallel with each other and in parallel with the electronic circuit, and iv) wherein the first transient voltage suppressor comprising the first and second unidirectional diodes is a permanently active circuit.

2. The implantable lead of claim 1, wherein the lead comprises a probe, a catheter, or a leadwire connected to an active medical device.

3. The implantable lead of claim 1, wherein the lead is either temporarily or permanently implantable in a human body.

4. The implantable lead of claim 1, wherein the electronic circuit comprises a frequency selective diverter or an impeder circuit.

5. The implantable lead of claim 4, wherein the frequency selective diverter or impeder circuit comprises an electronic filter.

6. The implantable lead of claim 5, wherein the electronic filter is selected from the group consisting of a passive low pass filter, an L-C trap filter, and a bandstop filter.

7. The implantable lead of claim 1, wherein the electronic circuit is selected from the group consisting of a micro electrical-mechanical switch (MEMS), a passive electronic switch, an active electronic switch, an electronic multiplexer, and a diode switch.

8. The implantable lead of claim 1, wherein the first transient voltage suppressor is selected from the group consisting of a diode, a zener diode, a transorb, a surge protector, and varistor components.

9. The implantable lead of claim 1, wherein at least one of the first and second diodes comprises a zener diode.

10. The implantable lead of claim 1, wherein the electronic circuit comprises a capacitor having a first electrode plate separated from a second electrode plate by a dielectric material.

11. The implantable lead of claim 10, wherein the dielectric material comprises a varistor dielectric material.

12. The implantable lead of claim 1, comprising a hermetic container in which the electronic circuit is disposed.

13. The implantable lead of claim 1, comprising a hermetic container in which the first transient voltage suppressor is disposed.

14. The implantable lead of claim 1 wherein the lead includes a therapy delivery electrode or a sensing electrode, and wherein the electronic circuit is located adjacent to or within the therapy delivery electrode or the sensing electrode.

15. The implantable lead of claim 14, wherein the therapy delivery or sensing electrode comprises a tip electrode and a ring electrode.

16. The implantable lead of claim 14, wherein the therapy delivery electrode or sensing electrode comprises a neurostimulator.

17. The implantable lead of claim 1, wherein the electronic circuit and the first transient voltage suppressor comprise discrete components physically arranged in series, but electronically connected in parallel.

18. The implantable lead of claim 17, wherein the electronic circuit comprises a discrete capacitor and a discrete inductor physically arranged in series, but electronically connected in parallel to thereby form a bandstop filter.

19. The implantable lead of claim 18, wherein the first diode is physically arranged in series with the capacitor and the inductor, but electronically connected in parallel to each of them.

20. The implantable lead of claim 19, wherein the second diode is physically arranged in series with the first diode, the capacitor and the inductor, but electronically connected in parallel to each of them.

21. The implantable lead of claim 17, comprising a hermetic container in which the electronic circuit and the first transient voltage suppressor are disposed.

22. The implantable lead of claim 1, including a second transient voltage suppressor disposed adjacent to the first lead wire proximal end.

23. The implantable lead of claim 22, wherein the second transient voltage suppressor comprises a fast-acting switch.

24. The implantable lead of claim 1 wherein one of the first and second diodes serves to forward conduct a positive pulse portion of a biphasic shock wave and the other of the first and second diodes serves to forward conduct a negative portion of the biphasic shock wave to thereby help protect the parallel connected electronic circuit from the biphasic shock wave.

25. An implantable lead configured to be disposed within a living body, the implantable lead comprising:

a) a first lead wire portion extending from a first lead wire portion proximal end to a first lead wire portion distal end and a second lead wire portion extending from a second lead wire portion proximal end to a second lead wire portion distal end, wherein the first lead wire portion proximal end is electrically connectable to a medical device;

b) an electronic circuit comprising a circuit first end and a circuit second end, wherein the circuit first end is electrically connected to the first lead wire portion distal end at a first node and the circuit second end is electrically connected to the second wire portion proximal end at a second node to thereby electrically connect the electronic circuit in series with the first and second lead wire portions; and c) a first diode electrically connected in parallel with a second diode between the first and second nodes to thereby provide a transient voltage suppressor electrically connected in parallel with the electronic circuit between the first and second nodes, d) wherein the first diode is configured to only permit the passage of a positive electrical pulse along the lead from the first lead wire portion proximal end to the second lead wire portion distal end while the second diode is configured to only permit the passage of a negative electrical pulse along the lead from the first lead wire portion proximal end to the second lead wire portion distal end, and e) wherein the first transient voltage suppressor comprising the first and second unidirectional diodes is a permanently active circuit.

26. An implantable lead configured to be disposed within a living body, the implantable lead comprising:
a) a first lead wire portion extending from a first lead wire portion proximal end to a first lead wire portion distal end and a second lead wire portion extending from a second lead wire portion proximal end to a second lead wire portion distal end, wherein the first lead wire portion proximal end is electrically connectable to a medical device;
b) an electronic circuit comprising a circuit first end and a circuit second end, wherein the circuit first end is electrically connected to the first lead wire portion distal end at a first node and the circuit second end is electrically connected to the second wire portion proximal end at a second node to thereby electrically connect the electronic circuit in series with the first and second lead wire portions; and
c) a first diode electrically connected in parallel with a second diode between the first and second nodes to thereby provide a transient voltage suppressor electrically connected in parallel with the electronic circuit between the first and second nodes,
d) wherein the first diode is biased in a forward direction opposite that of he second diode, and
e) wherein the first transient voltage suppressor comprising the first and second unidirectional diodes is a permanently active circuit.

27. An implantable lead, comprising:
a) a lead wire extending from a lead wire proximal end to a lead wire distal end electrically connected to an electrode;
b) an electronic circuit comprising a circuit first end and a circuit second end, wherein the circuit first end is electrically connectable to a medical device at a first node and the circuit second end is electrically connected to the lead wire proximal end to thereby electrically connect the electronic circuit in series with the lead wire; and
c) a transient voltage suppressor electrically connected in parallel with the electronic circuit, wherein the transient voltage suppressor comprises:
i) a first unidirectional diode having first P and N ends and a second unidirectional diode having second P and N ends,
ii) wherein the P end of the first diode is electrically connected at the first node to the N end of the second diode and to the electronic circuit first end, and
iii) wherein the N end of the first diode is electrically connected at the second node to the P end of the second diode and to the electronic circuit second end to thereby provide the first and second diodes in parallel with each other and in parallel with the electronic circuit, and
iv) wherein the first transient voltage suppressor comprising the first and second unidirectional diodes is a permanently active circuit, and
d) wherein one of the first and second diodes serves to forward conduct a positive pulse portion of a biphasic shock wave and the other of the first and second diodes serves to forward conduct a negative portion of the biphasic shock wave to thereby help protect the parallel connected electronic circuit from the biphasic shock wave.

28. An implantable lead, comprising:
a) a lead wire extending from a lead wire proximal end to a lead wire distal end, wherein the lead wire proximal end is electrically connectable to a medical device;
b) an electronic circuit comprising a circuit first end and a circuit second end, wherein the circuit first end is electrically connected to the lead wire distal end at a first node and the circuit second end is electrically connected to an electrode; and
c) a transient voltage suppressor electrically connected in parallel with the electronic circuit, wherein the transient voltage suppressor comprises:
i) a first unidirectional diode having first P and N ends and a second unidirectional diode having second P and N ends,
ii) wherein the P end of the first diode is electrically connected at the first node to the N end of the second diode and to the electronic circuit first end, and
iii) wherein the N end of the first diode is electrically connected at the second node to the P end of the second diode and to the electronic circuit second end to thereby provide the first and second diodes in parallel with each other and in parallel with the electronic circuit, and
iv) wherein the first transient voltage suppressor comprising the first and second unidirectional diodes is a permanently active circuit, and
d) wherein one of the first and second diodes serves to forward conduct a positive pulse portion of a biphasic shock wave and the other of the first and second diodes serves to forward conduct a negative portion of the biphasic shock wave to thereby help protect the parallel connected electronic circuit from the biphasic shock wave.

* * * * *